United States Patent [19]
Kleks et al.

[11] Patent Number: 5,350,410
[45] Date of Patent: Sep. 27, 1994

[54] AUTOCAPTURE SYSTEM FOR IMPLANTABLE PULSE GENERATOR

[75] Inventors: Jonathan A. Kleks, Northridge; Stuart W. Buchanan, Saugus; Raymond J. Wilson, Palmdale; John W. Poore, South Pasadena; Brian M. Mann, Beverly Hills, all of Calif.

[73] Assignee: Siemens Pacesetter, Inc., Sylmar, Calif.

[21] Appl. No.: 980,941

[22] Filed: Nov. 23, 1992

[51] Int. Cl.⁵ .......................................... A61N 1/362
[52] U.S. Cl. ........................................ 607/28; 607/11
[58] Field of Search .................... 607/28, 27, 13, 11

[56] References Cited

U.S. PATENT DOCUMENTS

| | | | |
|---|---|---|---|
| 3,777,762 | 12/1973 | Nielsen | 128/419 |
| 3,949,758 | 4/1976 | Jirak | 128/419 |
| 4,000,461 | 12/1976 | Barber et al. | 324/102 |
| 4,552,152 | 11/1985 | Hartlaub | 128/702 |
| 4,625,730 | 12/1986 | Fountain et al. | 128/419 |
| 4,674,508 | 6/1987 | DeCote | 128/419 |
| 4,674,509 | 6/1987 | DeCote, Jr. | 128/419 |
| 4,686,988 | 8/1987 | Sholder | 128/419 |
| 4,708,142 | 11/1987 | DeCote, Jr. | 128/419 |
| 4,708,144 | 11/1987 | Hamilton et al. | 128/419 |
| 4,712,555 | 12/1987 | Thornander et al. | 128/419 |
| 4,729,376 | 3/1988 | DeCote, Jr. | 128/419 |
| 4,809,697 | 3/1989 | Causey, III et al. | 128/419 |
| 4,817,605 | 4/1989 | Sholder | 128/419 |
| 4,878,497 | 11/1989 | Callaghan et al. | 607/28 |
| 4,913,146 | 4/1990 | DeCote, Jr. | 128/419 |
| 4,940,052 | 7/1990 | Mann et al. | 128/419 |
| 4,944,299 | 7/1990 | Silvian | 128/419 |

OTHER PUBLICATIONS

Feld, Gregory M.D. et al., "A New Pacemaker Algorithm for Automatic Threshold Determination and Capture Verification", Pace, vol. 14, p. 728; NASPE Abstracts (Apr. 1991, Part II).

Curtis, Anne B. M.D. et al., "A New Algorithm for Minimizing Pacemaker Polarization Artifact that is Universally Applicable in Permanent Pacing Systems", PACE, vol. 14, p. 728; NASPE Abstracts (Apr. 1991, Part II).

Primary Examiner—Angela D. Sykes
Assistant Examiner—Kennedy J. Schaetzle
Attorney, Agent, or Firm—Bryant R. Gold; Lisa P. Weinberg; Malcolm J. Romano

[57] ABSTRACT

An autocapture system within an implantable pulse generator automatically maintains the energy of a stimulation pulse at a level just above that which is needed to effectuate capture. The electrical post-stimulus signal of the heart following delivery of a stimulation pulse is compared to a polarization template, determined during a capture verification test. A prescribed difference between the polarization template and the post-stimulus signal indicates capture has occurred. Otherwise, loss of capture is presumed, and a loss-of-capture routine is invoked that increases the energy a prescribed amount to obtain capture. Periodically, and/or at programmed intervals or events, the capture verification test is performed. During the capture verification test, the pulse generator determines a polarization template for a particular stimulation energy and for each of a plurality of sensitivity or threshold settings. A determination is also made as to which sensitivity settings yield capture. An autocapture routine extends the capture verification test data to a wide range of stimulation energies. An autothreshold routine automatically sets the energy of the stimulation pulse a specified level above the energy at which capture is first lost.

34 Claims, 12 Drawing Sheets

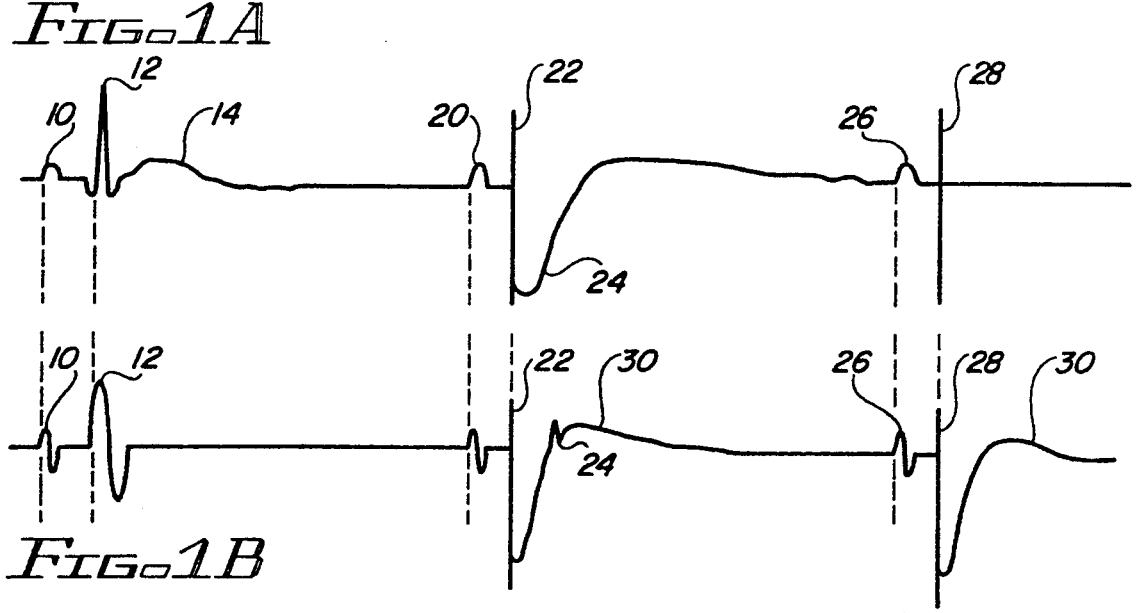
FIG.1A
FIG.1B
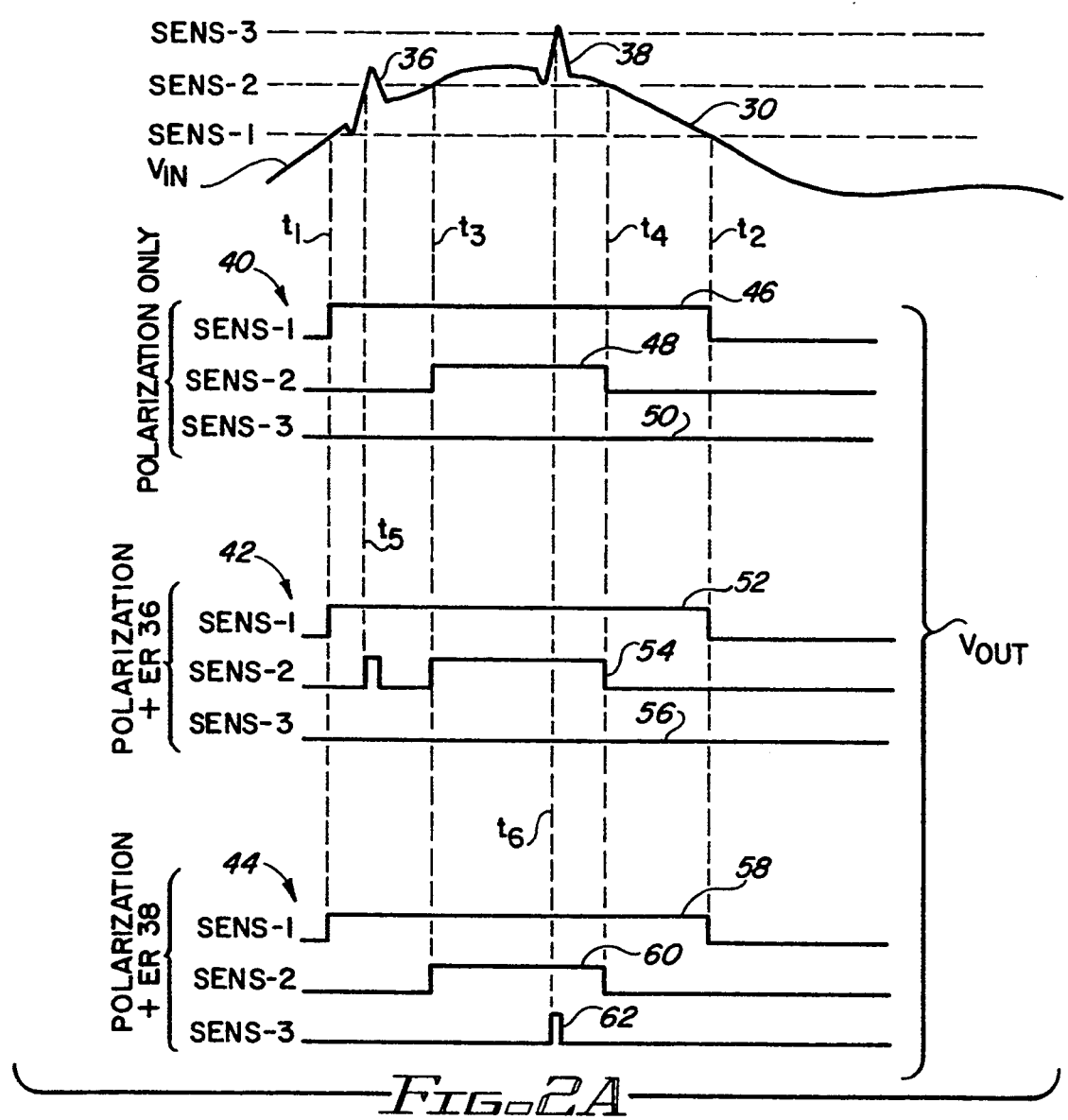
FIG.2A

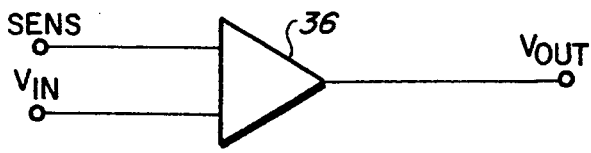
FIG. 2B
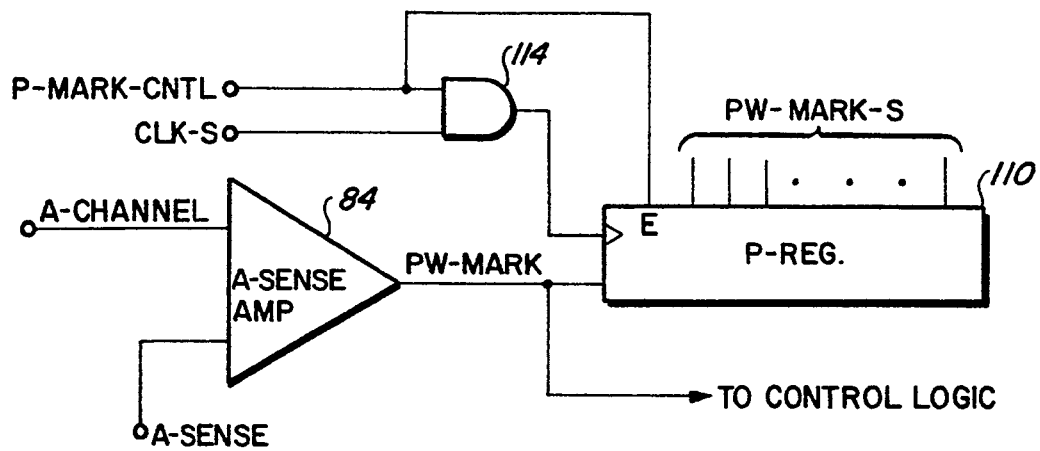
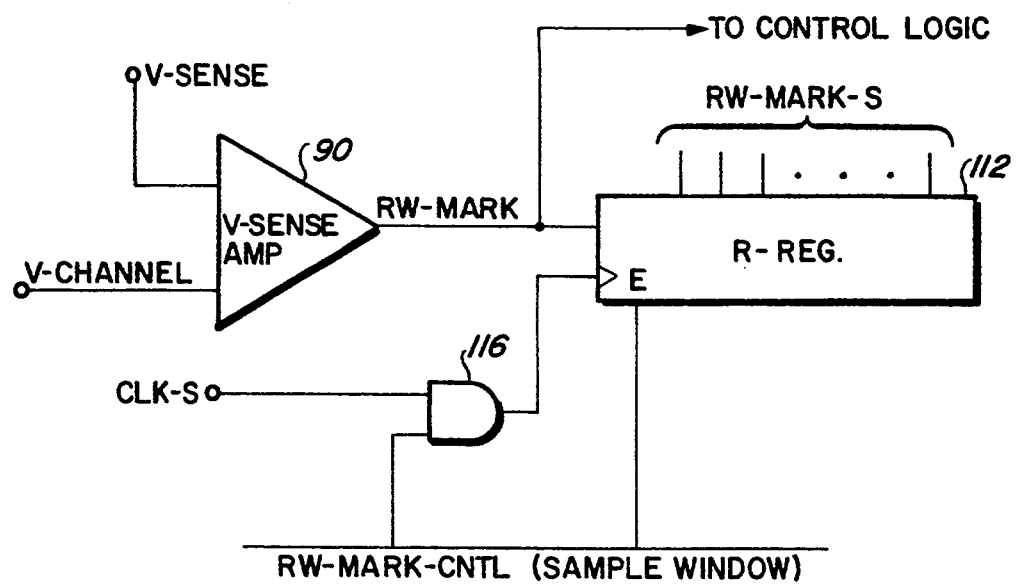
FIG. 4

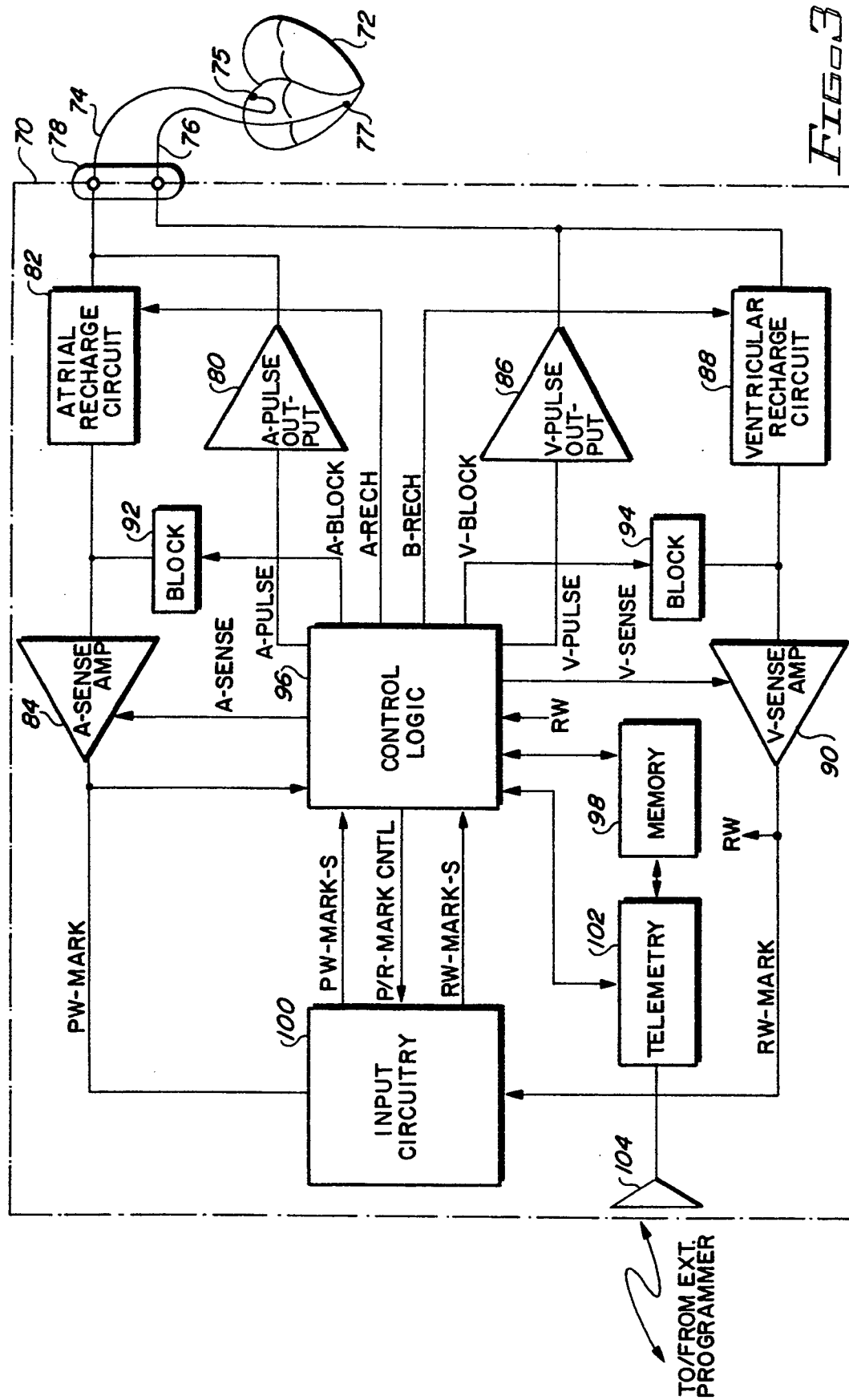

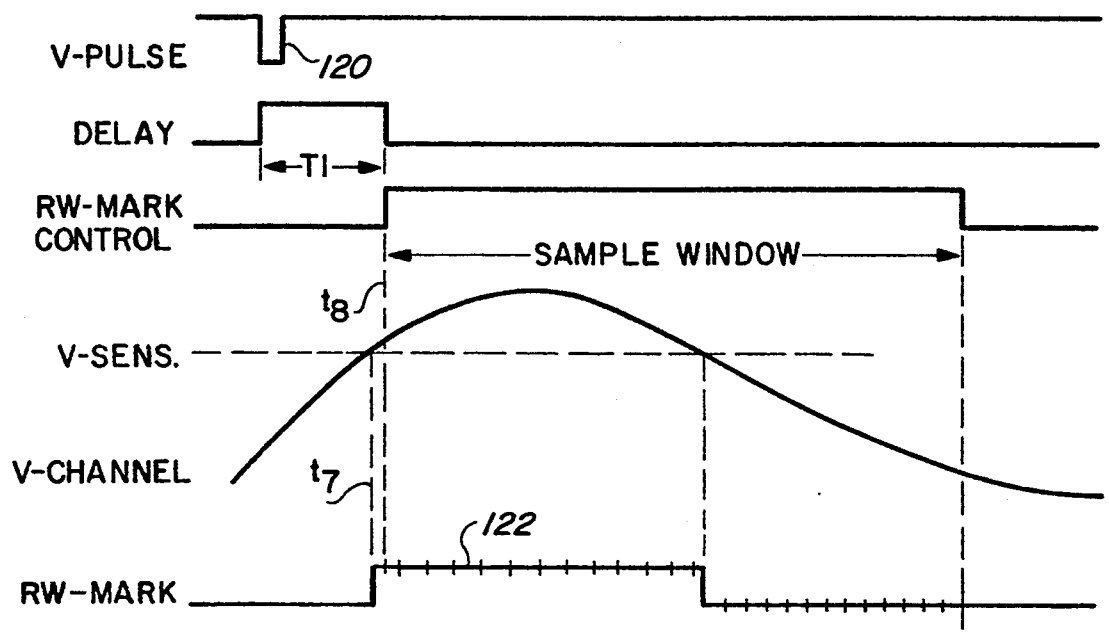
_FIG. 5_
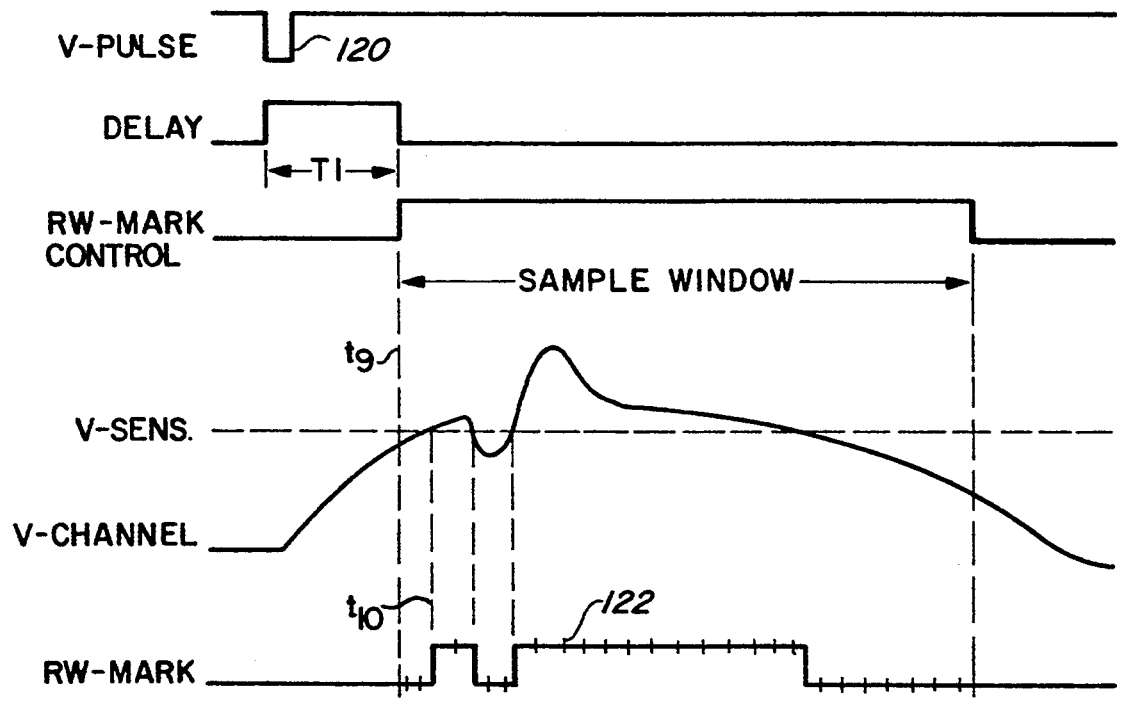
_FIG. 6_

FIG. 14

| PA VOLTS | PW MSEC | SENS. INDEX.MV | | 2ND PULSE (POLARIZATION) POLAR TEMP(i) | SINGLE PULSE PW/RW-MARK-S MARK(i) | ⊕ DIFF(i) | CAPTURE CAP(i) |
|---|---|---|---|---|---|---|---|
| 0.5 | 0.2 | 0. 1. 2. 3. 4. 5. 6. 7. | 30 25 15 10 8 6 4 2 | 0 0 0 0 0 0 0 0 0 0 0 1 0 1 0 0 1 1 0 0 1 1 − − 1 − − − 1 − − − − − − 1 − − − 1 − − − 1 − − − | 0 0 0 0 0 0 0 0 0 0 0 0 1 0 0 0 0 1 0 1 1 0 0 0 1 1 0 0 − 1 1 0 0 − − 1 1 − − − 1 − − − − − − | 0 0 0 0 0 0 0 0 0 0 0 0 1 0 0 0 0 1 1 0 0 0 0 1 0 1 0 1 1 0 0 0 1 0 1 0 0 0 0 0 0 0 0 0 0 0 0 0 | 0 0 (NO) 1 (YES) 0 0 0 (NO) 0 0 |
| 1.0 | 0.2 | 0. 1. 2. 3. 4. 5. 6. 7. | 30 25 15 10 8 6 4 2 | 0 0 0 0 0 0 0 0 0 0 1 1 0 0 0 0 1 0 1 0 0 0 − 1 0 0 − − − 1 − − − − − − 1 − − − − − − | 0 0 0 0 0 0 0 0 0 0 1 0 0 0 0 1 − 1 0 0 0 − − 1 0 − − − 1 − − − − − 1 − − − − − − | 0 0 0 0 0 0 0 0 0 1 0 1 0 0 0 0 1 0 1 0 0 1 0 0 0 1 − 1 0 0 0 0 0 1 0 0 0 0 0 0 0 0 0 0 0 | 0 0 (NO) 1 (YES) 0 1 0 0 0 0 |
| 1.5 | 0.2 | 0. 1. 2. 3. 4. 5. 6. 7. | 30 25 15 10 8 6 4 2 | 0 0 1 0 0 0 0 0 0 0 1 0 1 0 0 0 1 0 0 1 0 0 − 1 0 − − − 1 − − − − − 1 − − − − − − | 0 0 1 0 0 0 0 0 0 1 0 1 0 0 0 1 0 0 1 0 0 − 1 0 0 − − 1 − − − − − − 1 − − − − − − | 0 0 1 0 0 0 0 0 0 0 1 0 1 0 0 0 0 1 0 0 1 0 0 0 1 0 0 1 0 0 0 0 1 0 0 0 0 0 0 0 0 0 0 0 0 | 0 1 (NO) 1 (YES) 0 0 0 0 0 |
| 1.5 | 0.4 | 0. 1. 2. 3. 4. 5. 6. 7. | 30 25 15 10 8 6 4 2 | 0 0 1 1 0 0 0 0 0 0 1 0 1 0 0 0 1 0 0 1 0 − − 1 0 0 − − 1 − − − − − 1 − − − − − − | 0 0 1 0 0 0 1 0 1 0 1 0 0 0 − 1 0 0 − − 1 − − − − − − 1 − − − − − − − − − − | 0 0 1 0 1 0 0 0 0 0 1 1 0 0 0 0 0 1 0 0 1 0 1 0 0 0 1 0 0 0 0 0 0 0 0 0 0 0 0 0 0 0 0 0 0 | 0 1 (NO) 1 (YES) 0 0 0 0 0 |

AUTOCAPTURE SYSTEM FOR IMPLANTABLE PULSE GENERATOR

FIELD OF THE INVENTION

The present invention relates to implantable medical devices and methods, and more particularly to a system and/or method for use within an implantable pacemaker to automatically determine if a given stimulation pulse has effectuated capture. Further, the invention relates to a system and/or method that automatically adjusts the energy of the stimulation pulse so that it will always efficiently effectuate capture, i.e., so that it contains just enough energy to effectuate capture without expending significant energy over that needed for capture.

BACKGROUND OF THE INVENTION

A pacemaker is a medical device, typically implanted within a patient, that provides electrical stimulation pulses to selected chambers of the heart, i.e., the atrium and/or the ventricle. Such stimulation pulses cause the muscle tissue of the heart (myocardial tissue) to depolarize and contract, thereby causing the heart to beat at a controlled rate.

Most pacemakers can be programmed to operate in a demand mode of operation, i.e., to generate and deliver stimulation pulses to the heart only when the heart fails to beat on its own. To this end, the pacemaker senses cardiac activity, i.e., heart beats, and if the heart beats do not occur at a prescribed rate, then stimulation pulses are generated and delivered to an appropriate heart chamber, either the atrium or the ventricle, in order to force the heart to beat.

When operating in a demand mode of operation, the pacemaker defines a period of time, referred to generally as the "escape interval" (which may further be referred to as either an "atrial escape interval" or a "ventricular escape interval," depending upon the mode of operation of the pacemaker) that is slightly longer than the period of time between normal heart beats. Upon sensing such a "natural" (non-stimulated or non-paced) heart beat within the allotted time period, the escape interval is reset, and a new escape interval is started. A stimulation (or pacing) pulse will be generated at the conclusion of this new escape interval unless a natural heart beat is again sensed during the escape interval. In this way, stimulation pulses are generated "on demand," i.e., only when needed, in order to maintain the heart rate at a rate that never drops below the rate set by the escape interval.

The heart rate is monitored by examining the electrical signals that are manifest concurrent with the depolarization or contraction of the myocardial tissue. The contraction of atrial muscle tissue is manifest by the generation of a P-wave. The contraction of ventricular muscle tissue is manifest by the generation of an R-wave (sometimes referred to as the "QRS complex"). The sequence of electrical signals that represent P-waves, followed by R-waves (or QRS complexes) can be sensed from inside of or directly on the heart by using sensing leads implanted inside or on the heart, e.g., pacemaker leads; or by using external electrodes attached to the skin of the patient.

All modern implantable pacemakers are programmable. That is, the basic escape interval (atrial and/or ventricular) of the pacemaker, as well as the sensitivity (threshold level) of the sensing circuits used in the pacemaker to sense P-waves and/or R-waves, as well as numerous other operating parameters of the pacemaker, may be programmably set at the time of implantation or thereafter to best suit the needs of a particular patient. Hence, the pacemaker can be programmed so as to yield a desired performance.

The operation of a pacemaker as described above presupposes that a stimulation pulse generated by the pacemaker effectuates capture. As used herein, the term "capture" refers to the ability of a given stimulation pulse generated by a pacemaker to cause depolarization of the myocardium, i.e., to cause the heart muscle to contract, or to cause the heart to "beat." A stimulation pulse that does not capture the heart is thus a stimulation pulse that may just as well have not been generated, for it has not caused the heart to beat. Such a non-capturing stimulation pulse not only represents wasted energy—energy drawn from the limited energy resources (battery) of the pacemaker—but worse still provides the pacemaker logic circuits with false information. That is, heretofore the logic circuits of the pacemaker presuppose that each stimulation pulse generated by the pacemaker captures the heart. If the stimulation pulse does not capture the heart, then the pacemaker logic circuits are controlling the operation of the pacemaker based on false information, and may thus control the pacemaker in an inappropriate manner. There is thus a critical need for a way of determining whether a given stimulation pulse has effectuated capture.

While there are many factors that influence whether a given stimulation pulse effectuates capture, a principal factor is the energy of the stimulation pulse. The energy of the stimulation pulse, in turn, is determined by the amplitude and width of the stimulation pulse generated by the pacemaker. Advantageously, in a programmable pacemaker, both the amplitude and pulse width of the stimulation pulse are parameters that may be programmably controlled or set to a desired value.

An implantable pacemaker derives its operating power, including the power to generate a stimulation pulse, from a battery. The power required to repeatedly generate a stimulation pulse dominates the total power consumed by a pacemaker. Hence, to the degree that the power associated with the stimulation pulse can be minimized, the life of the battery can be extended and/or the size and weight of the battery can be reduced. Unfortunately, however, if the power associated with a stimulation pulse is reduced too far, the stimulation pulse is not able to consistently effectuate capture, and the pacemaker is thus rendered ineffective at performing its intended function. There is thus a continual need in the pacemaker art for a system and/or method for adjusting the energy of a stimulation pulse to an appropriate level that provides sufficient energy to effectuate capture, but does not expend any significant energy beyond that required to effectuate capture.

Heretofore, the most common technique used to adjust the stimulation energy to an appropriate level has been manually, using the programmable features of the pacemaker. That is, at the time of implant, the cardiologist or other physician conducts some preliminary stimulation tests to determine how much energy a given stimulation pulse must have to effectuate capture at a given tissue location. If the preliminary tests indicate that the capture threshold is high (compared to the average patient) then the lead will be repositioned until a "good" threshold is found. Once it has been determined that the thresholds are good, the stimulation electrode is then left in place and the amplitude and/or width of the stimulation pulse is set to a level that is typically 2 to 3 times greater than the amplitude and/or width determined in the preliminary tests. The increase in energy above and beyond the energy needed to effectuate capture is considered as a "safety margin."

During the acute phase, e.g., over a period of days or weeks after implant, the stimulation pulse energy needed to effectuate capture usually changes. This stimulation pulse energy is hereafter referred to as the "capture-determining threshold." Hence, having a safety margin factored into the stimulation pulse energy allows the stimulation pulses generated by the pacemaker to continue to effectuate capture despite changes in the capture-determining threshold. Unfortunately, however, much of the energy associated with the safety margin represents wasted energy, and shortens the life of the pacemaker's battery. Furthermore, after the acute phase (when the lead is considered in the chronic phase), the capture determining threshold is typically much lower than that determined at implant. If left unchecked, the safety margin determined necessary at implant is extremely wasteful during the chronic phase. What is needed, therefore, is a means of regularly checking the capture-determining threshold and adjusting the stimulation pulse energy accordingly so that energy is not needlessly wasted in a safety margin that is excessively large.

A common technique used to determine if capture has been effectuated is to look for an evoked response (ER) following a stimulation pulse. The "evoked response" is the response of the heart that results from the application of a stimulation pulse to the heart. When capture occurs, the evoked response is an intracardiac P-wave or R-wave (which typically has a different morphology, or wave shape, than does a P-wave or R-wave resulting from natural cardiac contractions) that indicates contraction of the respective cardiac tissue in response to the applied stimulation pulse. For example, using such evoked response technique, if a stimulation pulse is applied to the ventricle (hereafter referred to as a V-Pulse), any response sensed by the ventricular sensing circuits of the pacemaker immediately following the application of the V-Pulse is assumed to be an evoked response that evidences capture of the ventricles. Similarly, if a stimulation pulse is applied to the atrium, which pulse is referred to hereafter as an A-Pulse, any response sensed by the atrial sensing circuits of the pacemaker immediately following the application of the A-Pulse is assumed to be an evoked response that evidences capture of the atria.

One problem with evoked response detection is that the signal sensed by the ventricular and/or atrial sensing circuits immediately following the application of a V-Pulse and/or A-Pulse may not be an evoked response. Rather, it may be noise, either electrical noise caused, for example, by electromagnetic interference (EMI), or myocardial noise caused by random myocardial or other muscle contractions (muscle "twitching"). Alternatively, that which is sensed by the ventricular and/or atrial sensing circuits may be a natural R-wave or P-wave that just happens to occur immediately following the application of the non-capturing V-Pulse or A-Pulse.

Another signal that interferes with the detection of an evoked response, and potentially the most difficult to deal with because it is usually present in varying degrees, is lead polarization. Lead polarization is caused by electrochemical reactions that occur at the lead/tissue interface due to the application of the electrical stimulation pulse, A-Pulse or V-Pulse, across such interface. (The lead/tissue interface is that point where the electrode of the pacemaker lead contacts the cardiac tissue. Such point is normally inside the atrium or the ventricle, assuming endocardial stimulation leads are employed.) Unfortunately, because the evoked response is sensed through the same electrode through which the A-Pulse or V-Pulse is delivered, the resulting polarization signal also present at such electrode can corrupt the evoked response sensed by the sensing circuits of the pacemaker. To make matters worse, the lead polarization signal is not easily characterized. It is a complex function of the lead materials, lead geometry, tissue impedance, stimulation energy, and many other variables, most of which are continually changing over time.

In each case, the result is the same—a false positive detection of the evoked response. Such false positive detection thus leads to a false capture indication, which in turn can lead to missed heartbeats, a highly undesirable situation. What is needed, therefore, is a technique for clearly distinguishing a true evoked response from other signals that may occur at the same time as an evoked response, but are not an evoked response. What is needed, therefore, is a technique for eliminating, or at least minimizing, the adverse effect that lead polarization has on the ability of the pacemaker sensing circuits to sense the evoked response.

It is known in the art to generate stimulation pulses in pairs separated by a time less than the natural refractory period of the heart. (The natural refractory period of the heart is that time period following depolarization or contraction of the cardiac tissue during which the cardiac tissue is not capable of depolarizing again. Such natural refractory period, which may be thought of as a repolarization period, may vary from 100–200 msec or more.) The two-pulse approach uses the first stimulation pulse to effectuate capture wherein the signal measured immediately thereafter includes both the lead polarization and the evoked response. The second stimulation pulse does not effectuate capture (because the heart muscle tissue is not capable of contracting at that point in time) and the signal measured immediately thereafter is assumed to include only the lead polarization. The teaching of the prior art is that the signal measured after the second (non-capturing) pulse provides a measure of the lead polarization, which measure can then be electronically subtracted from the signal measured after the first (capturing) pulse to provide a true measure of the evoked response. See U.S. Pat. Nos. 4,674,508; 4,674,509; 4,708,142; 4,729,376; and 4,913,146, all issued to Robert DeCote, Jr.

There are two problems with the technique described in the DeCote, Jr. patents. First, it assumes that the "post-pulse lead recovery artifacts are essentially completely decayed within 50 msec. following the end of each pacing pulse," which is not universally true. Second, the invention by DeCote, Jr. requires an excessive amount of circuitry (e.g., an unsaturable sense amplifier, an A/D converter, an absolute value substractor, a digital integrator, a digital comparator, in addition to, threshold determination and control circuitry for carrying out the algorithm). Operation of this additional circuitry on a beat by beat basis simply draws too much current drain and can severely deplete the limited battery supply. Thus, there is a need for a system or technique whereby the evoked response signal can still be reliably sensed even in the presence of large polarization signals while requiring low power consumption. The present invention addresses the above and other needs.

SUMMARY OF THE INVENTION

The present invention provides an implantable pacemaker that includes an autocapture system for automatically maintaining the energy of the stimulation pulses generated by the pacemaker at a predetermined level safely above that needed to effectuate capture. The autocapture system performs its function by comparing the electrical evoked response of the heart following the generation of a stimulation pulse to a polarization template. If a prescribed difference exists between the polarization template and the evoked response, capture is presumed. If not, loss of capture is presumed, and a loss-of-capture routine is automatically invoked that increases the stimulation energy a prescribed amount in order to effectuate capture.

Periodically, and/or at programmed intervals or upon the occurrence of specified events, a capture verification test is performed. During such capture verification test, capture verification data is generated for a prescribed stimulation energy. Such capture verification data includes a definition of the polarization template corresponding to each of a plurality of sensitivity settings (i.e., gain settings of the sense amplifier) that may be used at the prescribed stimulation energy. The capture verification data also includes an indication as to whether capture occurs at the prescribed stimulation energy for each of the sensitivity settings. From this data, an optimum sensitivity setting for the prescribed stimulation energy may be selected in accordance with prescribed selection criteria. In doing so, the pacemaker is effectively biasing the sense amplifiers to an appropriate level for detecting an evoked response. Advantageously, the sense amplifiers used in the present invention are conventional, low powered sense amplifiers that are already present in all pacemakers.

During the capture verification test, the autocapture system causes the pacemaker to first generate a series of dual stimulation pulses, or pacing pulse pairs. The first pulse of the pair has a high energy to ensure capture. The second pulse of the pair is of the prescribed stimulation energy. The signal corresponding to the second pulse (which signal is dominated by polarization information) is sensed through a sensing circuit having a specified sensitivity (gain) setting. Such signal is stored as the polarization template corresponding to that particular energy and sensitivity setting. The process is then repeated for all of the applicable sensitivity settings of the sensing circuit for the particular stimulation energy, thereby creating a table of polarization templates as a function of sensitivity settings for that particular stimulation energy. Single stimulation pulses are then generated at the prescribed energy setting. The evoked response associated with each single stimulation pulse, as sensed through the sensing circuit for each of the plurality of specified sensitivity gain settings, is compared with the corresponding polarization template. If a prescribed difference exists between the evoked response and the polarization template, capture is presumed for that energy and threshold setting; if not, capture is not presumed for such settings.

The autocapture system of the present invention further includes means for automatically calibrating the system periodically and/or at prescribed intervals or events over a prescribed set of stimulation energies. After such autocalibration is performed, there is thus a complete set of capture verification data for all stimulation energies and sensitivity settings of interest, including a polarization template for each energy/sensitivity setting, an indication of whether a given energy/sensitivity setting effectuates capture, and an optimum sensitivity setting selected for each stimulation energy.

The autocapture system of the invention also includes an autothreshold means for adjusting (periodically and/or at prescribed intervals or events) the stimulation energy downward in an ordered sequence, starting from an initial high energy to ensure capture and decreasing in prescribed amplitude/pulse width combinations until capture is first lost. The autothreshold means then automatically sets the stimulation energy a prescribed amount above such loss-of-capture level, which prescribed amount may be considered as a "safety margin." Optimum control parameters associated with the stimulation energy at such safety-margin level may then be selected for use by the pacemaker.

In accordance with one aspect of the invention, the comparison between the evoked response and the polarization template is performed digitally, after converting the evoked response and template to corresponding digital words containing a prescribed number of bits. Such digital conversion is performed, in one embodiment, by sampling the analog evoked response at a prescribed sampling rate, and setting a digital bit at each sample time to one value if the analog evoked response is greater than a prescribed threshold level, and to another value if the analog evoked response is less than the prescribed threshold level. Such digital conversion may thus be considered as a single bit analog-to-digital (A/D) conversion, with the single bit being set at each sample time as a function of whether the analog evoked response is above or below the prescribed threshold. A collection of such single bits as a function of time thus comprises the digital words used to represent the evoked response or the polarization template. The comparison of the evoked response digital word to the polarization template digital word may then be performed using simple digital comparison circuitry, e.g., an Exclusive OR gate, that compares the bits of the two words on a bit-by-bit basis.

In another embodiment, the digital conversion is performed using an A/D converter that provides multiple bit resolution at each sample time. Hence, a digital word representative of the magnitude of the evoked response is obtained at each sample time. A collection of such digital words as a function of time thus comprises a digital signature (where a signature = multiple words) that represents the evoked response or the polarization template. The comparison of the evoked response signature to the polarization template signature may thus be performed using a conventional digital processor using conventional digital processing and numerical analysis techniques.

It is thus a feature of the present invention to provide a way to determine whether a given stimulation pulse generated by a pacemaker has effectuated capture.

It is another feature of the invention to provide a system and/or method for adjusting the energy of a stimulation pulse to an appropriate level that provides sufficient energy to effectuate capture, but does not expend any significant energy beyond that required to effectuate capture, thereby always pacing with a safety margin that is not excessively large.

It is a related feature of the invention to provide an implantable pacemaker that includes circuitry for regularly checking the capture-determining threshold and adjusting the stimulation pulse energy and sensitivity settings accordingly so that energy is not needlessly wasted in a safety margin that is excessively large.

It is an additional feature of the invention to provide a technique for clearly distinguishing a true evoked response from other signals that may occur at the same time as an evoked response, but are not an evoked response.

It is yet a further feature of the invention to provide a technique for eliminating, or at least minimizing, the adverse effect that lead polarization has on the ability of the pacemaker sensing circuits to sense an evoked response.

It is still another feature of the invention to provide a system or technique whereby the evoked response signal can be reliably sensed even when inextricably intertwined with a difficult-to-characterize polarization signal.

BRIEF DESCRIPTION OF THE DRAWINGS

The above and other aspects, features and advantages of the present invention will be more apparent from the following more particular description thereof, presented in conjunction with the following drawings wherein:

FIG. 1A shows a representative surface ECG waveform for an intrinsic beat, a paced beat which captures the heart, and a non-capturing paced beat.

Fig. 1B shows an intracardiac (EGM) electrogram waveform corresponding to the surface ECG shown in FIG. 1A, illustrating the problem that polarization creates for detecting an evoked response;

FIG. 2A schematically depicts the polarization portion of a typical intracardiac EGM waveform, and illustrates the effect of adjusting the sensitivity of a sense amplifier relative to sensing or not sensing the polarization and/or an evoked response that is coincident with the polarization;

FIG. 2B is a simplified diagram of the sense amplifier used in the present invention;

FIG. 3 is a block diagram of a pacemaker that includes the autocapture system of the present invention;

FIG. 4 is a block diagram of the input circuitry shown in FIG. 3;

FIG. 5 is a timing waveform diagram that illustrates the operation of the input circuitry for an EGM waveform that includes only polarization;

FIG. 6 is a timing waveform diagram as in FIG. 5 that illustrates the operation of the input circuitry for an EGM waveform that includes both polarization and an evoked response;

FIG. 14 depicts an example of the type of data used and generated in carrying out the capture verifiability test of FIGS. 13A and 13B.

DETAILED DESCRIPTION OF THE INVENTION

Figure 7:
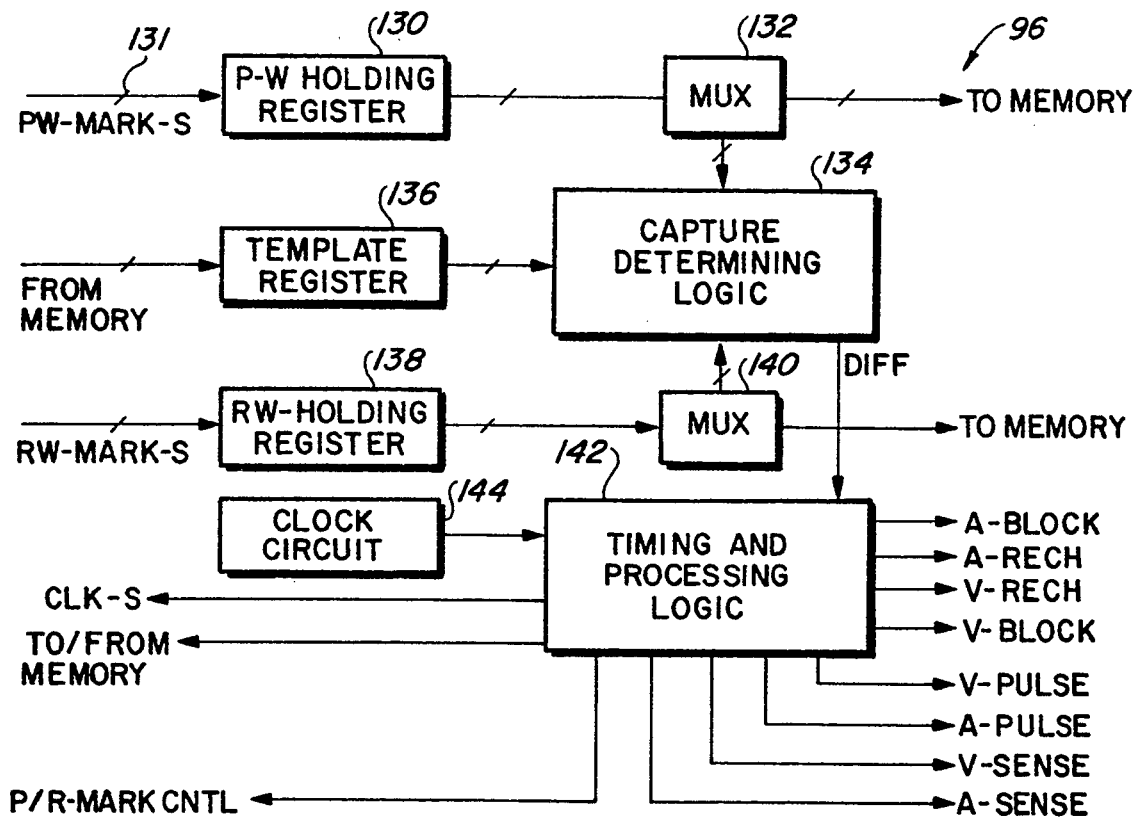
FIG. 7 is a block diagram of one embodiment of the control logic shown in FIG. 3.

The following description is of the best mode presently contemplated for carrying out the invention. This description is not to be taken in a limiting sense, but is made merely for the purpose of describing the general principles of the invention. The scope of the invention should be determined with reference to the claims. Corresponding reference characters indicate corresponding components throughout the several views of the drawings.

In FIG. 1A, there is shown a representative surface ECG waveform for an intrinsic beat, a paced beat that captures the heart, and a non-capturing paced beat. (For illustration purposes, the ECG waveform is that waveform sensed by skin electrodes positioned over the heart.) The ECG of an intrinsic heart beat includes a P-wave 10, evidencing the contraction of the atria of the heart; followed by an R-wave 12 (sometimes referred to as the QRS complex) evidencing contraction of the ventricles. A T-wave 14 follows the R-wave 12, evidencing the re-polarization of the ventricular muscle tissue. (It is noted that a T-wave 14 may or may not be evident in an ECG waveform such as is shown in FIG. 1A. However, for purposes of the present invention, the presence or absence of the T-wave is not important). This cycle, of a P-wave followed by an R-wave, evidencing the contraction of first the atria and then the ventricles, up to the time of the next P-wave, constitutes one cardiac cycle, or one heart beat. An ECG waveform of a healthy heart is thus made up of a continuing sequence of such waves: P-waves 10 followed by R-waves 12.

FIG. 1A further shows a representative ECG waveform for a paced heart, i.e., a heart to which a stimulation pulse has been applied in order to effectuate the contraction of the myocardial muscle tissue of a desired heart chamber. Thus, as seen in FIG. 1A, a P-wave 20 is followed by a ventricular stimulation pulse 22, or V-pulse 22. If of sufficient energy, the V-pulse 22 causes the ventricular muscle tissue to contract, as evidenced by the inverted R-wave 24. The inverted R-wave 24 thus represents the desired "evoked response" from the heart (as seen on a surface ECG) following application of a stimulation pulse. This process continues, i.e., a stimulation pulse 22 is generated as often as necessary to assure that a desired heart rate is maintained. As indicated previously, a stimulation pulse that elicits the desired evoked response 24 and causes the desired contraction is said to "capture" the heart. Following the inverted R-wave 24 is another P-wave 26 and a V-pulse 28 (as seen on an ECG recording) which does not capture the heart. For a more thorough description of the waveforms evidencing a beating or paced heart, and the basic configuration of an implantable pacemaker, including the basic block diagrams of the circuitry within an implantable pacemaker, see, e.g., U.S. Pat. Nos. 4,686,988; 4,712,555; 4,940,052; and 4,944,299, which patents are incorporated herein by reference.

FIG. 1B shows an intracardiac electrogram (EGM) waveform corresponding to the surface ECG shown in FIG. 1A, illustrating the problem that polarization creates for detecting an evoked response. (For purposes of the present application, the intracardiac EGM waveform is that waveform sensed by stimulation leads connected directly to heart, not by skin electrodes positioned over the heart.) For illustration purposes, the intracardiac signals for the P-wave 10 and the R-wave 12 are represented as bipbasic waveforms in FIG. 1B. In reality, the signals are highly dependent on the lead configuration (unipolar or bipolar) and the position and orientation of the electrodes along the depolarization wavefront, and may in fact be monophasic. The signal following stimulation pulse 22 in FIG. 1B is a representation of an intracardiac evoked R-wave 24 in the presence of lead polarization 30. As described above, lead polarization is caused by electrochemical reactions that occur at the lead/tissue interface due to the application of the electrical stimulation pulse, i.e., the A-Pulse or V-Pulse, across such interface. Lead polarization is represented FIG. 1B as a large, wide artifact 30 that begins immediately after the application of a V-pulse 22. The size of the polarization artifact 30 is a function of the lead material, the load and the stimulation energy delivered. Typically, the polarization signal is "large" relative to the amplitude of the R-wave 24 which is on the order of 10–25 mV. Without the active removal of charge on the lead, the polarization signal would completely swamp out the evoked response. Note that as illustrated in FIG. 1B, the V-pulse 22 captures the heart as evidenced by the evoked response 24. However, the subsequent V-pulse 28 does not capture the heart, as evidenced by the presence of the lead polarization 30 without an evoked response following the V-pulse.

The present invention advantageously provides a technique or system for determining if capture occurs (i.e., if an evoked response is present) following application of a stimulation pulse, regardless of whether a lead polarization artifact is present.

It should be emphasized that the polarization artifact 30 shown in FIG. 1B is only representative of what such an artifact may look like. Indeed, one of the difficulties associated with the existence of the polarization artifact 30 is that it is so difficult to characterize, frequently changing its overall shape and size. Unfortunately, because the evoked response 24 is sensed through the same electrode through which the A-Pulse or V-Pulse is delivered, the resulting polarization artifact or signal 30 is also present at such electrode, and its presence can corrupt the evoked response sensed by the sensing circuits of the pacemaker.

To better understand how the presence of the lead polarization signal 30 complicates the detection of the evoked response 24 using the sensing circuits of a pacemaker, reference is next made to FIGS. 2A and 2B. FIG. 2A shows the polarization artifact 30 of a typical intracardiac EGM waveform. Such signal 30, which may or may not include an evoked response, is applied to one input of a sense amplifier 36, shown schematically in FIG. 2B, as an input signal $V_{IN}$. Another input to the sense amplifier 36 is a sensitivity signal, labeled "Sens" in FIG. 2B. For purposes of the present invention, the sensitivity signal, Sens, may be considered as a threshold signal that sets the level above which the input signal $V_{IN}$ must rise before the input signal is amplified or otherwise processed by the sense amplifier 36. Thus, only when the input signal $V_{IN}$ exceeds the sensitivity signal, Sens, is an output signal, $V_{OUT}$, of the sense amplifier 36 generated. The output signal, $V_{OUT}$, may thus be considered as an amplified and filtered version of the those portions of the input signal, $V_{IN}$, that exceed the sensitivity signal, Sens.

Those of skill in the pacing art will recognize that considering the sensitivity signal as a threshold signal is somewhat of an oversimplification. That is, the sense amplifier 36 has characteristics similar to those of an operational amplifier, having feedback compensation that provides a bandpass filter transfer function, and may also thus appear similar to a differentiator at certain frequencies. As configured in most pacemakers, the sensitivity signal not only sets a threshold above which the input signal must rise before it is acted upon by the sense amplifier, but also affects the gain and frequency response of the sense amplifier. However, for purposes of the present application, it is generally sufficient to consider the sensitivity signal, Sens, as a threshold-determining type of signal, and the sense amplifier as simply an amplifier that amplifies and filters those portions of the input signal that are greater than the sensitivity signal.

With reference to the waveforms shown in FIG. 2A, three possible sensitivity signals (threshold signals or levels) are shown in the top part of the figure relative to an input signal, $V_{IN}$. For purposes of explanation, the input signal, $V_{IN}$, includes the polarization signal 30, a first evoked response 36 and a second evoked response 38, with the evoked responses 36 and 38 being positioned at two possible time intervals on the polarization signal 30. The three possible sensitivity signals are identified as Sens-1, Sens-2, and Sens-3.

FIG. 2A shows the output signal, $V_{OUT}$, that would be obtained under three different conditions. The first condition, shown generally at 40, is with respect to only the polarization signal 30. That is, the first condition 40 assumes that the evoked responses 36 and 38 are not present. The second condition, shown generally at 42, is with respect to the polarization signal 30 and the evoked response 36. That is, the second condition 42 assumes that only the polarization signal 30 and the evoked response 36 are present, not the evoked response 38. The third condition, shown generally at 44, is with respect to the polarization signal 30 and the evoked response 38. That is, the third condition 44 assumes that only the polarization signal 30 and the evoked response 38 are present, not the evoked response 36.

For the first condition 40—polarization only—it is seen in FIG. 2A that the output signal, $V_{OUT}$, assumes one of three possible waveforms depending upon which sensitivity signal is used. If the first sensitivity signal, Sens-1, is applied to the sense amplifier 36, then an output signal 46 is generated that is low until such time as the input signal waveform, $V_{IN}$, exceeds the Sens-1 threshold level, which occurs at time $t_1$, and remains high until such time as the input signal waveform, $V_{IN}$, drops below the Sens-1 threshold level, which occurs at time $t_2$. Note that the output waveform 46, and all the other output waveforms shown in FIG. 2A, assume that the sense amplifier 36 has sufficient gain to quickly saturate as soon as the input signal exceeds the threshold. Thus, the output waveform $V_{OUT}$ appears as a digital signal, assuming either a low value (when the input signal $V_{IN}$ in less than the sensitivity threshold) or a high value (when the input signal $V_{IN}$ is greater than the sensitivity threshold). Similarly, when the second sensitivity signal, Sens-2, is used, an output signal 48 is generated that is low until such time as the input signal waveform, $V_{IN}$, exceeds the Sens-2 threshold level, which occurs at time $t_3$, and remains high until such time as the input signal waveform, $V_{IN}$, drops below the Sens-2 threshold level, which occurs at time $t_4$. The third sensitivity signal, Sens-3, is above the polarization signal 30. Thus, when Sens-3 is used, an output signal 50 is generated that remains low the entire time.

For the second condition 42—polarization plus the evoked response 36—FIG. 2A shows that an output signal 52 is generated when the sensitivity signal Sens-1 is used that is the same as the output signal 46 described above. When the sensitivity signal Sens-2 is used, in contrast, an output signal 54 is generated that momentarily goes high at time $t_5$, corresponding to when the evoked response 36 momentarily exceeds the threshold level set by Sens-2. The output signal 54 again goes high when the polarization signal 30 exceeds the Sens-2 threshold level, at time $t_3$, and remains high until the polarization signal drops below the Sens-2 threshold level at time $t_4$. Again, when the sensitivity signal Sens-3 is used, the input signal (made up of the polarization signal 30 and the evoked response 36) never exceeds the threshold level set by the Sens-3 signal. Thus, the resulting output signal, 56, remains low the entire time.

For the third condition 44—polarization plus the evoked response 38—FIG. 2A shows that an output signal 58 is generated when the sensitivity signal Sens-1 is used that is the same as the output signal 46 and 52 described above. When the sensitivity signal Sens-2 is used, an output signal 60 is generated that is the same as the output signal 48 described above, i.e., going high at time $t_3$ and low at time $t_4$, corresponding to the times when the polarization signal 30 exceeds and then drops below the Sens-2 threshold level, respectively. In contrast, when the sensitivity signal Sens-3 is used, an output signal 62 is generated that momentarily goes high when the evoked response 38 momentarily exceeds the threshold level set by Sens-3, at time $t_6$.

FIG. 2A thus illustrates the effect of adjusting the sensitivity of the sense amplifier used in a pacemaker to a setting which indicates whether or not the polarization signal and/or an evoked response are sensed. Ideally, the sensitivity should be set so that the evoked response is detected, but the polarization is not. As seen in FIG. 2A, if the sensitivity is set too high, as exemplified by the Sens-1 signal, then the output signal, $V_{OUT}$, is the same regardless of whether an evoked response is present or not because the polarization signal 30 dominates that which is detected. Such a sensitivity setting is thus too sensitive to be of any value with respect to detecting an evoked response. In contrast, the sensitivity setting represented by the Sens-2 signal is set optimally relative to detecting the evoked response 36, but is too sensitive relative to not detecting the polarization signal 30. Thus, the polarization signal 30 still dominates and makes detection of the evoked response 38 difficult.

In a similar manner, the sensitivity setting represented by the Sens-3 signal is set optimally relative to detecting the evoked response 38, while being insensitive to detect the evoked response 36.

FIG. 2A thus highlights the problem of detecting the evoked response in the presence of the polarization signal. Only when the evoked response occurs at the peak of the polarization signal, as does the evoked response 38 in FIG. 2A, is there any hope of optimally setting the sensitivity threshold so as to detect only the evoked response and not the polarization signal. However, when the evoked response occurs at some other point on the polarization waveform, such as does the evoked response 36 in FIG. 2A, then it is virtually impossible to optimally set the sensitivity threshold so as to detect the evoked response and not detect the polarization signal. The present invention advantageously addresses this difficult problem and provides a technique for detecting the evoked response, regardless of whether a polarization signal is present, and regardless of where on the polarization curve the evoked response occurs.

The system used by the present invention to detect capture is referred to hereafter as an "autocapture" system. This is because, as will be evident from the description that follows, such system is able to automatically determine whether a given stimulation pulse has effectuated capture of the heart. Such knowledge is invaluable in the operation of a pacemaker because it provides a positive indication of that which has always been assumed before—that a given stimulation pulse did what it was intended to do, namely, cause a contraction of the heart. With such knowledge, the stimulation energy can be automatically increased, if needed, in order to assure that capture occurs; yet the total energy of the stimulation pulse can be automatically maintained at a level that is not overly excessive, i.e., at a level that is just slightly above that needed to effectuate capture, thereby preserving the limited energy reserves stored in the battery of the pacemaker.

To better understand the present invention, reference is next made to FIG. 3 where there is shown a block diagram of a pacemaker 70 that includes an autocapture system made in accordance with the invention. The pacemaker 70 is coupled to a heart 72 by way of stimulation leads 74 and 76. As depicted in FIG. 3, the lead 74 is an atrial lead, having an electrode 75 at its distal end that is in contact with atrial cardiac tissue; and the lead 76 is a ventricular lead, having an electrode 77 that is in contact with ventricular cardiac tissue. However, it is to be understood that the use of two stimulation leads, one for each chamber of the heart, is only exemplary, as the invention also has applicability to pacing systems that utilize only a single lead, as in a single chamber pacemaker, or to pacing systems that utilize more than two leads.

The atrial and ventricular leads 74 and 76 are electrically connected through a pacemaker connector 78 to electrical circuits within the pacemaker 70. The atrial lead 74, for example, is connected to an A-pulse output amplifier 80 and an atrial recharge circuit 82. The output of the atrial recharge circuit 82 is connected to an atrial sense amplifier, "A-sense Amp," 84. In like manner, the ventricular lead 76 is connected to a V-pulse output amplifier 86 and a ventricular recharge circuit 88, with the output of the ventricular recharge circuit 88 being connected to the input of a ventricular sense amplifier, "V-sense Amp," 90. Blocking circuitry 92 and 94 is coupled to the input of the A-sense amp 84 and the V-sense amp 90, respectively.

The sensitivity (threshold) of the A-sense amp 84 is set by a control signal, "A-sense," generated by control logic 96 (hereafter referred to as simply the "control logic"). Similarly, the sensitivity of the V-sense amp 90 is set by a control signal, "V-sense," also generated by the control logic 96.

As further shown in FIG. 3, a memory circuit 98 is coupled to the control logic 96. Also coupled to the control logic 96 is input circuitry 100. The memory 98 has stored therein various control parameters and variables. The input circuitry 100 receives and processes the signals sensed through the atrial and ventricular sense amplifiers 84 and 90 (e.g., the P-wave, the R-wave, or the evoked response). Such control parameters, variables, and sensed signals are used by the control logic 96 in controlling the operation of the pacemaker 70 in a prescribed manner.

The memory 98, as well as the control logic 96, are both coupled to a telemetry circuit 102. The telemetry circuit, through a suitable transmitter 104, or equivalent means for establishing a telecommunicative link, is able to communicate with a programming device external to the pacemaker 70. Thus, where the pacemaker 70 is implanted within a patient, the external programmer may be located external to the patient. Hence, through use of a suitable external programming device, the pacemaker may be "programmed" to operate in a desired manner simply by changing the control parameters and variables stored in the memory 98. For example, the sensitivity setting of the A-sense amp 84 may be selectively adjusted through use of such an external programming device. Further, data stored in the memory 98 that is accumulated during the operation of the pacemaker, such as event data, status data, EGM data, and the like, may be coupled to the external programming device for display and/or analysis through the telemetry circuit 102 and transmitter 104. See U.S. Pat. No. 4,809,697, incorporated herein by reference, for a more complete description of an external programmer and the manner in which it interfaces with an implantable pacemaker.

The basic operation of an implantable pacemaker is well documented, and will not be repeated herein. See, e.g., the above-referenced patents that have been incorporated herein by reference. The present invention is primarily concerned with determining when capture occurs. Thus, for purposes of the present invention, only the signals sensed by the A-sense amp 84 and/or the V-sense amp 90 after a stimulation pulse has been delivered by the A-pulse amplifier 80 and/or the V-pulse output amplifier 86 are of concern, and the following description is directed to such post stimulation pulse signals. It is to be understood, however, that all of the other signals associated with the operation of an implantable pacemaker, are also present.

One embodiment of the present invention may be characterized as an implantable pacemaker, such as the implantable pacemaker 70 shown in block diagram form in FIG. 3. Such implantable pacemaker includes a pulse generator (80 or 86) that generates a stimulation pulse at a selectable stimulation energy, and at least one stimulation lead (74 or 76) that electrically connects the pulse generator to a heart (72). Thus, it is through the stimulation lead that the stimulation pulse is delivered to the heart. The pacemaker further includes a sensing circuit (84 or 90) coupled to the stimulation lead. The sensing circuit senses an evoked response from the heart at a selectable sensitivity, determined by the control signals A-sense and/or V-sense. The pacemaker 70 also includes input circuitry (100) that converts the evoked response (ER) sensed by the sensing circuit (84 or 90) into an evoked response digital signal. A memory circuit (98) included in the pacemaker stores a plurality of control variables associated with the operation of the pacemaker. Such control variables include a polarization template. A control logic (96) coupled to the input circuitry and the memory circuit controls the operation of the pacemaker in a prescribed manner as determined by the plurality of control variables and a capture signal. Such control logic (96) includes a processor circuit that compares the polarization template to the evoked response digital signal and generates the capture signal only when a prescribed difference exists between the polarization template and the evoked response digital signal. Thus, in operation, the presence of the capture signal indicates that the heart was captured by the stimulation pulse delivered to the heart by the pulse generator (80 or 86), while the absence of the capture signal indicates that the heart was not captured by the stimulation pulse.

As mentioned above, the function of the input circuitry 100 is to convert the signal sensed by the sense amplifiers 84 or 90 after delivery of a stimulation pulse to a digital signal. Such digital signal is referred to above as an evoked response digital signal. FIG. 4 shows a block diagram of one embodiment of the input circuitry 100 that achieves this function.

Referring next to both FIGS. 3 and 4, the A-sense amp 84, and the V-sense amp 90 receive an input signal labeled "A-channel" and "V-channel," respectively. Such input signals are obtained from the output of the atrial recharge circuit 82 and the ventricular recharge circuit 88, respectively. Such signals may also be affected by the blocking circuits 92 or 94, respectively. That is, as is known in the pacemaker art, there are certain time periods, principally during and immediately following the delivery of a stimulation pulse, when it is necessary to have the sense amplifiers turned off, or to at least clamp the input signals to the sense amplifiers so that the sense amplifiers are protected from the large stimulation pulse that might otherwise appear at the input to the amplifier. The blocking circuits 92 and 94 (sometimes referred to as blanking circuits) are used for this purpose.

The A-sense amp 84 and the V-sense amp 90 also receive, as a control input, the sensitivity signal, A-sense or V-sense, respectively, as described previously. The output of the A-sense amp 84 is a signal that is labeled "PW-Mark" in FIG. 4. Similarly, the output of the V-sense amp 90 is a signal that is labeled "RW-Mark." For this embodiment, both the PW-Mark signal and the RW-Mark signal are essentially two level signals (high and low) as shown for $V_{OUT}$ in FIG. 2A because the sense amplifiers have sufficient gain to quickly saturate once the input signal exceeds the sensitivity threshold setting. During the normal operation of the pacemaker, when the pacemaker control logic 96 is waiting for a prescribed time period (generally referred to as the "escape interval") to determine if a natural heartbeat will occur, the PW-Mark signal (if any) and the RW-Mark signal (if any) are directed to the control logic 96 to indicate to the control logic that a P-wave or an R-wave has been detected.

As seen in FIG. 4, the PW-Mark signal is also directed to a P-Register 110, and the RW-Mark signal is also directed to a R-register 112. The P-register 110 is clocked by a clock signal, CLK-S, that is received through an AND gate 114, or equivalent, only when a P-Mark Control signal is present. The P-Mark Control signal, or an equivalent signal, is also used to enable/reset the P-register 110. Thus, for example, when the P-Mark Control signal is low, the P-register is not enabled and all of its contents are set to zero. When the P-Mark Control signal is high, the P-register is enabled, and the clock signal, CLK-S, is allowed to pass through the AND gate 114 to clock the enabled P-register 110. Hence, at the appropriate clock transition time, the value of the PW-Mark signal (high or low) is clocked into the P-register 110. At the next clock transition time, the value of the PW-Mark signal at that time is clocked into the P-register 110, and the previous value is shifted one bit location in the register. The contents of the P-register 110 thus comprise a multibit signal, labeled PW-Mark-S, where each bit represents a sample of the PW-Mark signal at a particular clock transition time.

Similarly, the R-register 112 is clocked by the clock signal CLK-S received through an AND gate 116, or equivalent, only when an R-Mark Control signal is present. Hence, when the R-register 112 is enabled, the clock signal, CLK-S, samples the RW-Mark signal and places the results of such sampling in the R-register 112. The contents of the R-register 112 thus comprise a multibit signal, labeled RW-Mark-S, where each bit represents a sample of the RW-Mark signal at a particular clock transition time.

As described above, the P-register 110 and the R-register 112, and the associated circuitry used therewith, comprise the input circuitry 100 that digitizes the PW-Mark and RW-Mark signals. Such digitizing is further illustrated in the timing waveform diagrams of FIGS. 5 and 6. Such figures show only the digitizing of the V-channel signal, i.e., as performed by the R-register 112, but it is to be understood that a similar process occurs relative to the A-channel. FIG. 5 shows the digitizing of the RW-Mark signal when it is made up of only a polarization signal (no evoked response); and FIG. 6 shows the digitizing of the RW-Mark signal when it is made up of both a polarization signal and an evoked response.

As seen in both FIGS. 5 and 6, following the delivery of a stimulation pulse, manifest by the presence of a V-pulse signal 120, a delay is generated of a prescribed time period T1 during which the R-Mark-Control signal is kept low, preventing the R-register 112 from sampling the RW-Mark signal. During a portion of this time, the V-sense amplifier 90 may be blanked, in conventional pacemaker fashion, to effectively turn OFF the V-sense amplifier. The time period T1 is a programmable time period that may be selected for each patient. Typically T1 will be around 10–20 msec.

After the delay period T1, a sample window begins during which the RW-Mark signal is sampled. The sample window is created by the RW-Mark Control signal described above in connection with FIG. 4. For the situation shown in FIG. 5, the sample window just happens to begin at time $t_8$, shortly after time $t_7$ when the V-channel input signal exceeds the V-Sense threshold level set by the V-sense amp sensitivity setting. For the situation shown in FIG. 6, the sample window just happens to begin at time $t_9$, shortly before time $t_{10}$ when the V-channel input signal first exceeds the V-Sense threshold level.

During the sample window, the RW-mark signal (which, as described in FIG. 2A, comprises a high or low signal depending upon whether the V-channel input signal is above or below the V-Sense threshold level) is sampled at the clock rate. The sample times are represented in FIGS. 5 and 6 by small vertical tick marks 122 placed along the RW-Mark signal. The sample time is determined by the clock rate, which in the preferred embodiment is in the range of 150 to 200 Hz. The sampling rate is selected so that a desired number of "bits" or samples are obtained for the selected sampling window duration. Thus, if the desired number of bits for the multibit RW-Mark-S signal is 16, and if the sampling window is 64 msec long, then the RW-Mark signal should be sampled every 4 msec, or at a rate of about 250 Hz. If desired, a faster sampling rate can be used, e.g., 25 KHz, resulting in sampling the RW-Mark signal every 40 $\mu$sec, and providing a much longer multibit RW-Mark-S signal (in terms of the number of bits). However, for processing purposes, such long multibit RW-Mark-S signal can be divided into segments, or signatures, with each segment being processed in an appropriate manner.

The RW-Mark signal shown in FIG. 5 corresponds to the situation where there is no evoked response, only a polarization signal. In accordance with the present invention, the digitized multibit RW-Mark-S signal obtained under such conditions (or the digitized multibit PW-Mark-S signal obtained under such conditions, if the atrial channel is used) is considered as a "polarization template." Such polarization template is stored in the memory 98 of the pacemaker, and is subsequently retrieved and compared to the multibit RW-Mark-S signal obtained when an evoked response is present, e.g., as shown in FIG. 6.

As seen in FIG. 6, when an evoked response is present, the RW-Mark signal will typically be significantly different than will the RW-Mark signal when an evoked response is not present. The degree of difference is largely a function of the sensitivity setting (which sets the location of the V-Sense threshold) and the magnitude of the evoked response. The present invention advantageously takes advantage of this fact and recognizes that capture has occurred only when a prescribed difference exists between the polarization template and the current multibit RW-Mark-S signal. It is to be understood that although the above description assumes a two-level bit signal, the signal for RW-Mark-S may include a multibit signal wherein finer discrimination of levels and polarity are possible, e.g., using an analog-to-digital converter.

FIG. 7 is a block diagram of one embodiment of the control logic 96 shown in FIG. 3. Such control logic 96 includes a PW-Holding Register 130 for receiving the multibit PW-Mark-S signal. (Note that the diagonal slash 131 going through the signal line leading to the PW-Holding register, and through most of the other signal lines shown in FIG. 7, represents a multibit bus. Such multibit buses may be, e.g., 16 or 32 bits wide.) Similarly, there is an RW-Wave Holding Register 138 for receiving the multibit RW-Mark-S signal; and a template register 136 for receiving and holding the polarization template stored in memory. Both the PW-Holding Register 130 and the RW-Holding Register 138 are coupled to multiplexers (Mux) 132 and 140, respectively. Such multiplexers function as switches that selectively direct the output of the respective holding register to either the memory 98 or to capture determining logic 134. (As those skilled in the art will recognize, FIG. 7 is a functional block diagram; and while it is convenient in such a diagram to show separate Mux's 132 and 140, in practice such Mux's may be realized using a single multi-input Mux.)

The capture determining logic 134 compares the current multibit PW-Mark-S signal, or the current multibit RW-Mark-S signal, to the appropriate polarization template, retrieved from memory and placed in the template register 136, in order to determine if there is a prescribed difference therebetween. Such a prescribed difference, as explained more fully below, may be determined simply by comparing the two digital signals on a bit-by-bit basis. If a prescribed number of the bits are different, then the two signals are deemed sufficiently different, and a difference signal, DIFF, is generated. The presence of the DIFF signal, which may be a single bit of a digital control word, thus provides an indication that a capture condition exists.

The DIFF signal is coupled to timing and processing logic 142. The timing and processing logic includes appropriate processing and logic circuitry, coupled to the memory 98, that generates the control signals used to operate the pacemaker 70. Clock circuit 144 generates the requisite clock signals needed by the timing and processing logic in order to carry out such function. For purposes of the present invention, such control signals include the V-pulse and A-pulse signals that trigger the generation of a ventricular and atrial stimulation pulse by the V-pulse output amplifier 86 and the A-pulse output amplifier 80, respectively; the sensitivity settings, V-sense and A-sense, used by the V-sense amp 90 and the A-sense amp 84, respectively; the A-Block and V-Block signals used to control the atrial block circuit 92 and the ventricular block circuit 94, respectively; the A-Rech and V-Rech signals used to control the Atrial recharge circuit 82 and the ventricular recharge circuit 88, respectively; and the P-Mark control and the R-Mark control signals (referred to collectively as the "P/R-Mark Cntl") used to define the sample window in the input circuitry 100.

As explained in connection with FIGS. 9–17 below, with knowledge of when capture has occurred, the timing and processing logic 142 may be programmed appropriately to automatically adjust the stimulation energy of the stimulation pulse, as required, in order to assure that capture always occurs, but at an energy level that is just above (by a modest safety margin) that needed to effectuate capture. Such action saves a significant amount of the limited energy reserves that are stored in the pacemaker, and thereby prolongs the useful life of the pacemaker.

As shown in FIG. 3, the atrial recharge circuit 82 and/or the ventricular recharge circuit 88 are used to control the charge that is allowed to build up on the pacemaker leads 74 or 76. In the absence of a stimulation pulse, such leads may collect a significant amount of charge thereon, much like a capacitor. In order to reduce the effects of such charge, and the adverse effect such charge can have on being able to sense cardiac activity, as well as on influencing the magnitude and shape of the polarization signal that is sensed at the pacemaker, the atrial and ventricular recharge circuits are used to discharge the stimulation leads at an appropriate time in the pacing cycle. Typically, such discharge time is immediately following the generation of a stimulation pulse. A more complete description of the recharge circuits may be found in several U.S. Patents see, for example, U.S. Pat. No. 4,406,286, filed Apr. 9, 1981, entitled "Fast Recharge Output Circuit," and U.S. Pat. No. 4,543,956, filed May 24, 1984, entitled "Biphasic Cardiac Pacer," which references are hereby incorporated herein by reference. Alternately, or in addition to the recharge circuitry, the present invention may be used together with sensing from the ring electrode to the pacemaker case.

Figure 8:
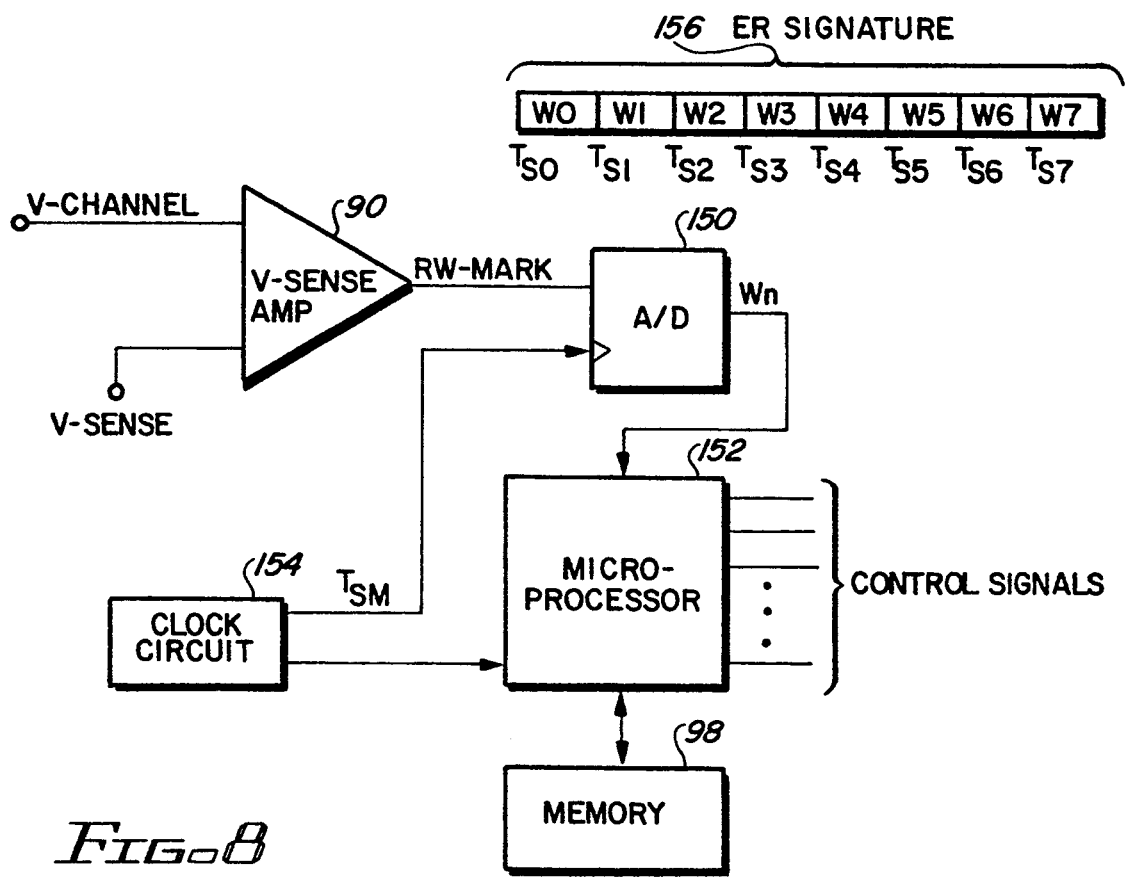
FIG. 8 is a block diagram of the ventricular channel of a microprocessor-based embodiment of the present invention.

Referring next to FIG. 8, there is shown a block diagram of the ventricular channel of a microprocessor-based embodiment of the present invention. (It is to be understood that an atrial channel could also be realized using a similar configuration.) It should be noted that the timing and processing logic 142 shown above in FIG. 7 may also include a microprocessor, or equivalent. However, the embodiment described above in connection with FIGS. 4–7 generally assumes that the multibit PW/RW-Mark-S signal (where the "PW/RW-Mark-S" signal is used to refer collectively to either the multibit PW-Mark-S signal, the multibit RW-Mark-S signal, or both) is generated as described above, i.e., by sampling the PW/RW-Mark signal at each sampling time and setting a bit of the resulting digital word as a function of whether the sampled value is above or below a prescribed threshold. In contrast, the embodiment shown in FIG. 8 uses an analog-to-digital converter (A/D) 150 that samples the RW-Mark signal at a sampling time $T_{sn}$ set by a sampling signal generated by a clock circuit 154. As a result of such a sample, the A/D converter, in conventional manner, converts the magnitude of the RW-Mark signal at the sampling time Tsn to a digital word, $W_n$, which digital word comprises a plurality of bits. Over a period of several sample times, the combination of such digital words, $W_n$, thus makes up a digital signature. Such a digital signature is shown in FIG. 8 as an "ER signature" 156. The ER signature 156 is made up of a first digital word, $W_0$, representing the magnitude of the RW-Mark signal at a sample time $T_{s0}$; a second digital word, $W_1$, representing the magnitude of the RW-Mark signal at a sample time $T_{s1}$; a third digital word, $W_2$, representing the magnitude of the RW-Mark signal at a sample time $T_{s2}$; and so on; up to an $n^{th}$ digital word, $W_n$, representing the magnitude of the RW-Mark signal at a sample time $T_{sn}$. While the ER signature 156 shown in FIG. 8 is an eight word signature, it is to be understood that this is only exemplary, as any length signature could be used.

Still referring to FIG. 8, it is seen that the ER signature 156 is delivered to a microprocessor 152. The microprocessor 152, in turn, is programmed in conventional manner using a program stored in memory 98, so as to process the ER signature 156 in an appropriate manner. Such processing follows the same general pattern as described elsewhere herein, i.e., a given ER signature 156 is compared to a polarization template signature on a word-by-word basis. If a predetermined difference exists between a prescribed number of the words making up the ER signature and the polarization template, then a capture condition is deemed to be present. Once a determination is made as to whether a given stimulation pulse has effectuated capture, then the microprocessor 152, or equivalent processing circuitry, can take whatever action is necessary to adjust and maintain the stimulation energy at a level that is not wasteful of the energy available in the battery of the pacemaker, but that is sufficient to capture the heart.

Advantageously, the present invention, whether made in accordance with the embodiment shown in FIGS. 4-7 or FIG. 8, may thus be considered as an autocapture system and/or an autocapture method for use within an implantable pacemaker. The implantable pacemaker used with such a system or method includes stimulation means for generating a stimulation pulse at a selectable stimulation energy and delivering such stimulation pulse to a heart; and sensing means for sensing an evoked response from the heart at a selectable sensitivity following delivery of the stimulation pulse. The autocapture system or method includes the following elements or steps: (a) means for defining a polarization template for a selected stimulation energy of the stimulation means and a selected sensitivity of the sensing means; (b) means for stimulating the heart with a stimulation pulse having the selected stimulation energy; (c) means for sensing an evoked response with the sensing means at the selected sensitivity; and (d) means for comparing the polarization template with the evoked response and indicating capture if a prescribed difference exists therebetween.

Coupled with the autocapture system summarized above, the present invention also includes a system and/or method for automatically adjusting the stimulation energy of an implantable pacemaker to a level that is a modest safety margin above the level required to effectuate capture. The implantable pacemaker used with such system and/or method includes stimulation means for generating a stimulation pulse at a selectable stimulation energy and delivering the stimulation pulse to a heart. Such auto-adjustment system and/or method includes the following elements or steps: (a) energy reduction means for reducing the stimulation energy by a prescribed amount; (b) capture verification means within the implantable pacemaker for verifying if capture exists at the reduced stimulation energy effectuated by the stimulation energy reduction means; (c) control means for: (1) incrementally reducing the stimulation energy with the energy reduction means until capture is no longer verifiable using the capture verification means, and then (2) increasing the stimulation energy by a prescribed safety margin.

The autocapture system and/or method of the present invention is carried out by programming the control logic 96 to selectively carry out four autocapture response functions as summarized in Table 1. Each of these functions may be considered as a particular mode of operation, or submode of operation for the pacemaker. Thus, when the autocapture system is enabled, or when operating in an autocapture mode, a calibration mode (AutoCalibration) may be invoked, as may a threshold mode (AutoThreshold), a capture verification mode, or a loss of capture mode.

Figure 9:
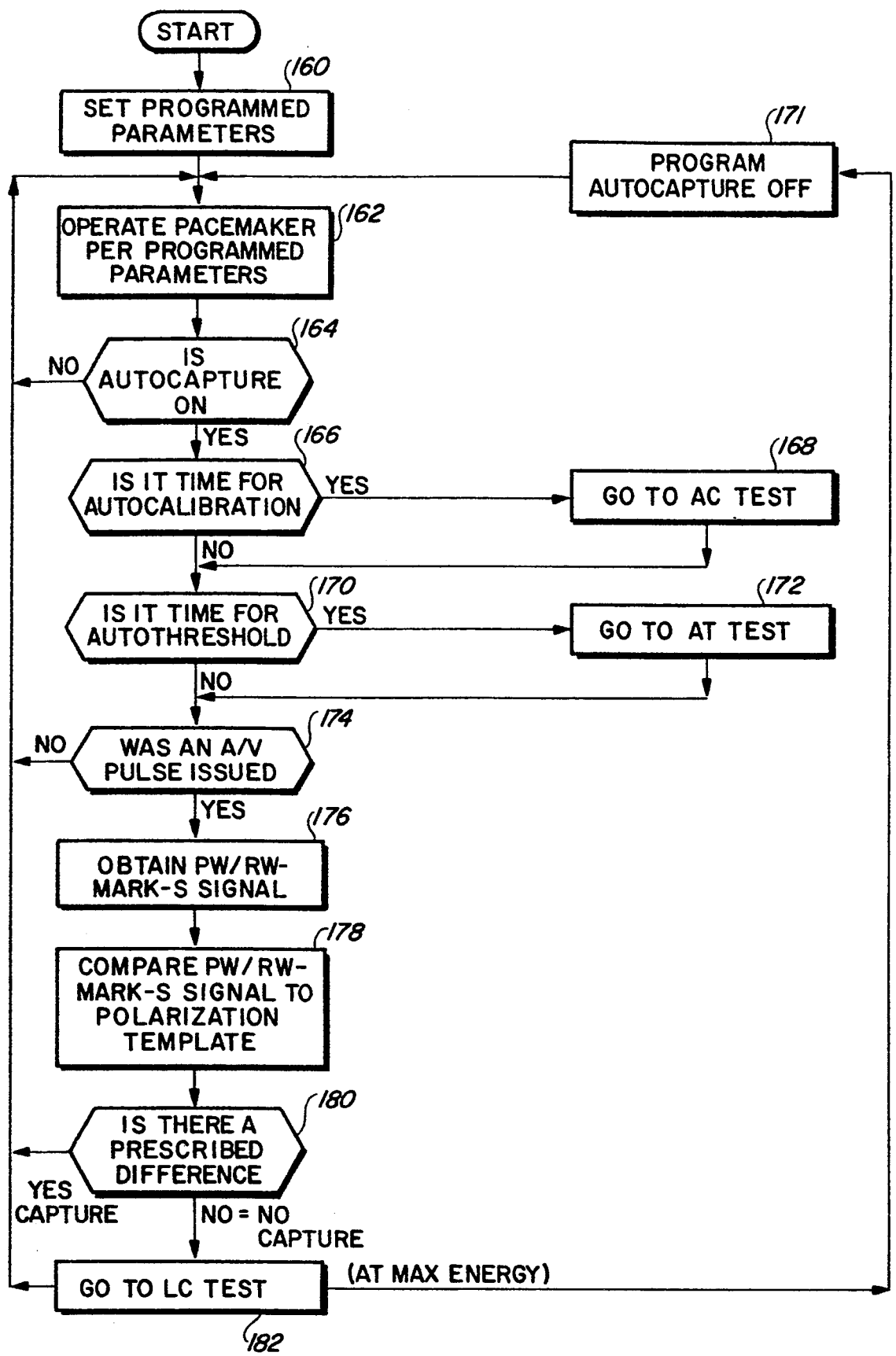
FIG. 9 shows a flowchart of the overall operation of the autocapture system of the present invention.
Figure 10:
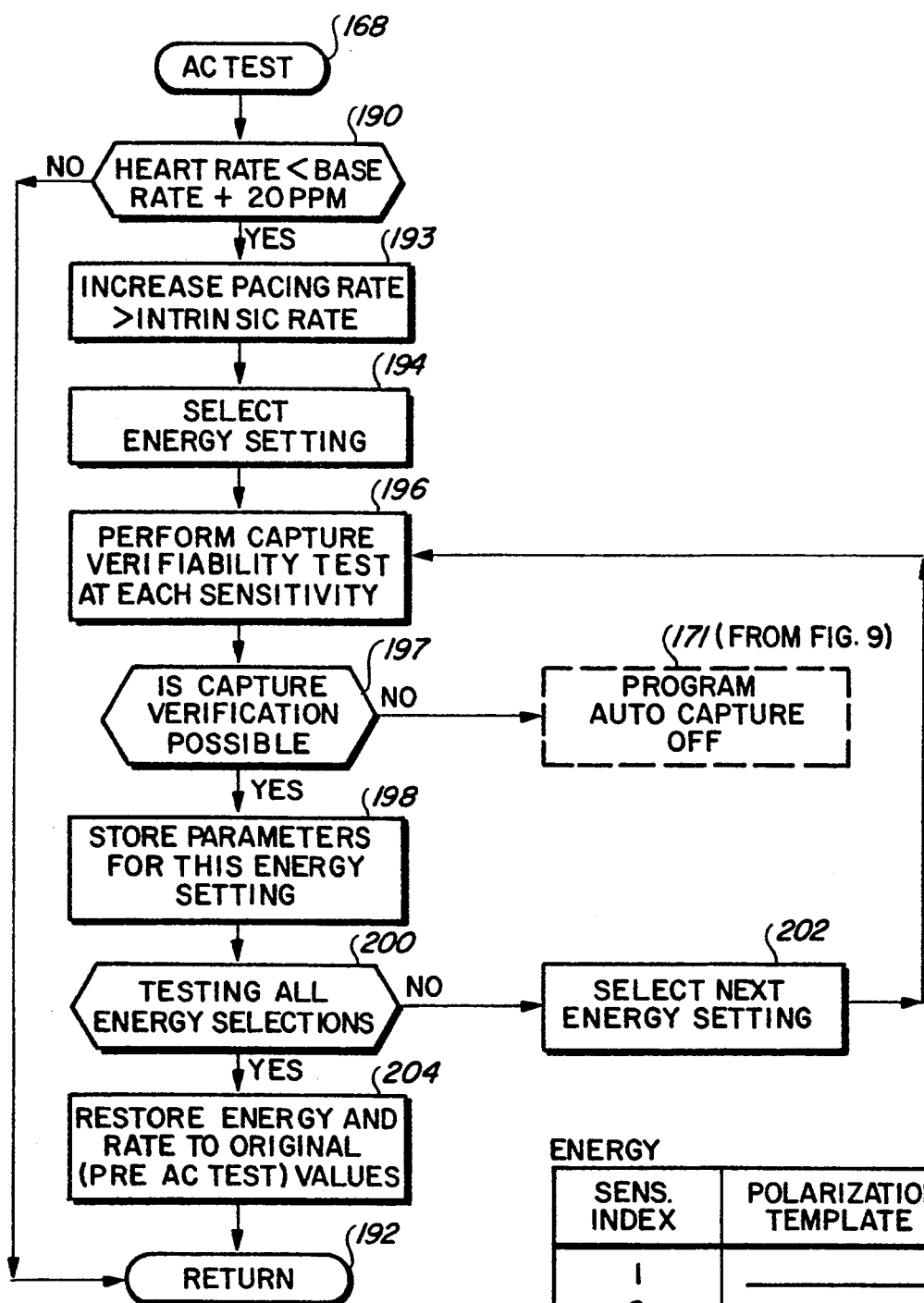
FIG. 10A shows a simplified flowchart of an autocalibration (AC) procedure carried out by the autocapture system shown in FIG. 9.
FIG. 10B shows a suggested table format for storing capture verification data.

A flowchart that depicts the overall operation of the autocapture system in accordance with one embodiment of the present invention is shown in FIG. 9. In such flowchart, and in the other flowcharts presented herein, each main step of the process being carried out is depicted in a separate "block" of the flowchart, with each block having a reference number attached thereto for explanation purposes. Thus, as seen in FIG. 9, a first step of the autocapture system requires that the programmed parameters be set (block 160). Such programmed parameters include, e.g., the desired pacing mode, the normal operating parameters associated with such programmed mode (such as the stimulation energy, the pacing rate, the sensitivity of the sense amplifier, electrode polarity, etc.) and the like. Further, if the pacemaker is a rate-responsive pacemaker, the programmed parameters will include the appropriate rate-responsive pacing parameters, such as a base rate, a slope, a maximum pacing rate, and the like. See, e.g., U.S. Pat. No. 4,940,052. For purposes of the autocapture system and method of the present invention, the programmed parameters include whether or not autocapture is ON (because there may be some patients and/or some instances where it would not be desirable to use the autocapture system); how often the AutoCalibration function and the AutoThreshold function (Table 1) should be automatically invoked, and the like.

TABLE 1

| AUTOCAPTURE RESPONSE FUNCTIONS | |
|---|---|
| Function Name | Brief Description |
| 1. Loss of Capture (LC) | Detects Loss of Capture; increases energy m steps. |
| 2. AutoCalibration (AC) | Invokes capture verification (CV) to generate table of capture verification data for all pacing energies. |
| 3. AutoThreshold (AT) | Reduces stimulation energy one step at a time until capture is lost, then invokes LC. |
| 4. Capture Verification (CV) | Generates capture verification data for a prescribed stimulation energy; determines optimum sensitivity setting for the prescribed energy. |

Notes:
m = 3 in preferred embodiment.

Once the programmed parameters have been set, the pacemaker operates in accordance with the programmed mode of operation, as controlled by the programmed parameters in conventional manner (block 162). As part of such programmed operation, a determination is made as to whether the autocapture feature has been programmed ON (block 164). If not, the programmed operation continues in a normal manner (block 162). If autocapture is ON, then a determination is next made as to whether it is time to perform the AutoCalibration function (block 166). The AutoCalibration function is briefly described in Table 1, above, and is described more fully below in conjunction with the description of FIG. 10A and 10B.

If it is time to carry out the AutoCalibration (AC) function (block 166), then such AutoCalibration function is carried out (block 168). There are two possible outcomes associated with the AutoCalibration function: (1) a successful outcome, in which case the autocapture system continues to the next step (block 170); or (2) an unsuccessful outcome, meaning that capture verification (CV) is not possible (block 169).

In one embodiment, if capture verification is not possible, then autocapture is automatically programmed to an OFF state (block 171), and the pacemaker returns to operating in its programmed mode (block 162) until the physician next interrogates the pacemaker. In a second embodiment, the autocalibration function is periodically invoked to determine whether the pacing environment (e.g., thresholds, lead impedance, etc.) has changed so that capture verification can be determined.

In yet another embodiment, the pacemaker system will automatically test all the electrodes available and determine the optimum electrode polarity (i.e., tip-to-ring, tip-to-case, or ring-to-case) for sensing post-stimulation signals prior to performing another AutoCalibration test. If an alternate optimum electrode configuration is found to be suitable for evoked response detection, then the pacemaker is programmed to that polarity for evoked response detection and AutoCalibration remains enabled. In this embodiment, the pulse generator generates stimulation pulses at a desired stimulation pulse energy using each of the electrode configurations. The system then determines the optimum sensitivity for each of the electrode configurations at the desired stimulation pulse energy, as described above. The control logic compares the optimum sensitivity for each of the electrode configurations, and selects as the optimum electrode configuration the electrode configuration having a difference signal, Diff(i), with the maximum number of bits set to "1". If an equal number of bits are set to "1", the system further looks for the Diff(i) signal having the highest sensitivity. The control logic then automatically programs the pacemaker's electrode configuration to the optimum electrode configuration and the optimum sensitivity for the desired stimulation pulse energy. For subsequent beat-by-beat detection, the system uses a selected polarization template corresponding to the optimum sensitivity, the desired stimulation pulse energy, and the optimum electrode configuration. The post-stimulus signals are then compared to the selected polarization template, and difference signal is produced, wherein a precribed difference signal indicates whether capture has occurred.

If AutoCalibration is carried out successfully, or if it is not yet time to perform the AutoCalibration function, the next step carried out by the autocapture system is to determine whether it is time to perform the AutoThreshold function (block 170). The AutoThreshold function is briefly described in Table 1, and is described more fully below in conjunction with the description of FIG. 11. Essentially, as seen in Table 1, the AutoThreshold function reduces the stimulation energy until capture is lost, and then invokes the Loss of Capture (LC) function, which function increases the stimulation energy by a prescribed safety margin.

After completing the AutoThreshold function, or if it is not yet time to perform the AutoThreshold function, the next step carried out by the autocapture system is to determine if an A-pulse or a V-pulse has been issued (block 174). If not, e.g., as when a normal P-wave or R-wave is sensed and a stimulation pulse is not needed, then the pacemaker continues to operate in its programmed mode of operation (block 162). If a stimulation pulse has been issued, then the multibit PW/RW-Mark-S signal is obtained using one of the approaches described above in conjunction with FIGS. 4-8, or equivalent (block 176). The multibit PW/RW-Mark-S signal is then compared to the particular polarization template that corresponds to the stimulation energy and sensitivity setting that is being used (block 178). If a prescribed difference exists between the polarization template and the multibit PW/RW-Mark-S signal, then capture has been achieved (block 180). If the prescribed difference does not exist, then capture has not occurred. In such instance, the Loss of Capture (LC) function is invoked (block 182).

Referring next to FIG. 10A, a simplified flowchart of the AutoCalibration (AC) procedure is illustrated. A first step of the AutoCalibration procedure involves making a determination as to whether the heart rate is less than or equal to the programmed base rate plus a small delta, which in the preferred embodiment is 20 ppm (block 190). (This determination assures that the test is performed when the heart rate is at a low rate because at lower rates the capture verification data is more meaningful.) If so, the AutoCalibration procedure continues. If not, the AutoCalibration procedure is not performed, and the procedure returns (block 192) to the main pacemaker operation (block 170 of FIG. 9). For example, a patient's base rate is typically programmed to 70 ppm because this is a natural resting rate for most people. A rate of 90 ppm typically indicates that the patient is now exercising. Thus, if the programmed base rate is 70 ppm, and if the heart rate is 88 ppm, then the AutoCalibration procedure will continue. However, if the heart rate were 92 ppm, then the AutoCalibration procedure would not go forward (92 ppm is greater than 70 +20 ppm (block 190)). Instead, the process would return to the main AutoCapture procedure set forth in FIG. 9 until the next timeout occurs for the AutoCalibration procedure to repeat itself. Thus, the AutoCalibration procedure will periodically be invoked and will, effectively, be suspended until the elevated heart rate is over.

If the heart rate is less than the base rate plus 20 (as determined at block 190), then the pacing rate is first increased to a rate greater than the intrinsic rate (block 193) in order to assure 100% pacing during the capture verifiability test, i.e., that any evoked response is as a result of the stimulation pulse and not the result of a natural heart beat. This may be achieved by either sensing the intrinsic rate and pacing slightly faster (say 5 ppm faster) or by arbitrarily pacing at a higher rate. For example, in the embodiment shown in FIG. 10A, the present invention will suspend the AutoCalibration procedure when the intrinsic rate is greater than the base rate plus 20 ppm. Thus, the pacing the heart at a rate equal to the base rate +20 ppm (block 193) will ensure 100% pacing.

Next, an initial energy setting is selected (block 194) for the stimulation pulse. Typically, such energy setting will be at the high end of a prescribed sequence of stimulation pulse energy settings for which the AutoCalibration procedure is to be performed. Examples of such energy setting sequences are shown in FIGS. 15-18 below.

Next, a capture verifiability test is performed at the selected energy setting (block 196). Such capture verifiability test is explained below in conjunction with FIGS. 13A and 13B. As a result of such test, a determination is made at block 197 whether: (1) capture verification is not possible; or (2) capture verification is possible. If the former, control of the AutoCalibration process reverts to block 171 (FIG. 9); if the latter, capture verification data for the selected energy setting are stored (block 198). Such capture verification data include a polarization template and a capture signal (or capture flag or bit) as a function of a sensitivity index. Such data may be stored in a table format, as suggested by the table format 199, shown in FIG. 10B.

After storing the capture verification data for the current stimulation energy setting (block 198), a determination is next made as to whether all energy settings associated with the prescribed sequence of energy settings have been tried (block 200). If not, then the next energy setting of the prescribed sequence is selected (block 202) and the process repeats (blocks 196, 198, 200). If so, then the stimulation energy and rate are restored to its pre-AutoCalibration value (i.e., that value of stimulation energy and base rate that was used prior to invoking the AutoCalibration procedure) (block 204), and the AutoCalibration procedure concludes by returning (block 192) to the main autocapture routine (block 170 of FIG. 9).

Thus, it is seen that the AutoCalibration procedure cycles through a prescribed sequence of stimulation energies, invoking a capture verifiability test at each energy in order to collect capture verification data for that stimulation energy. Hence, once the AutoCalibration procedure has been successfully carried out, there exists a table of capture verification data for all stimulation energies of interest.

Figure 11:
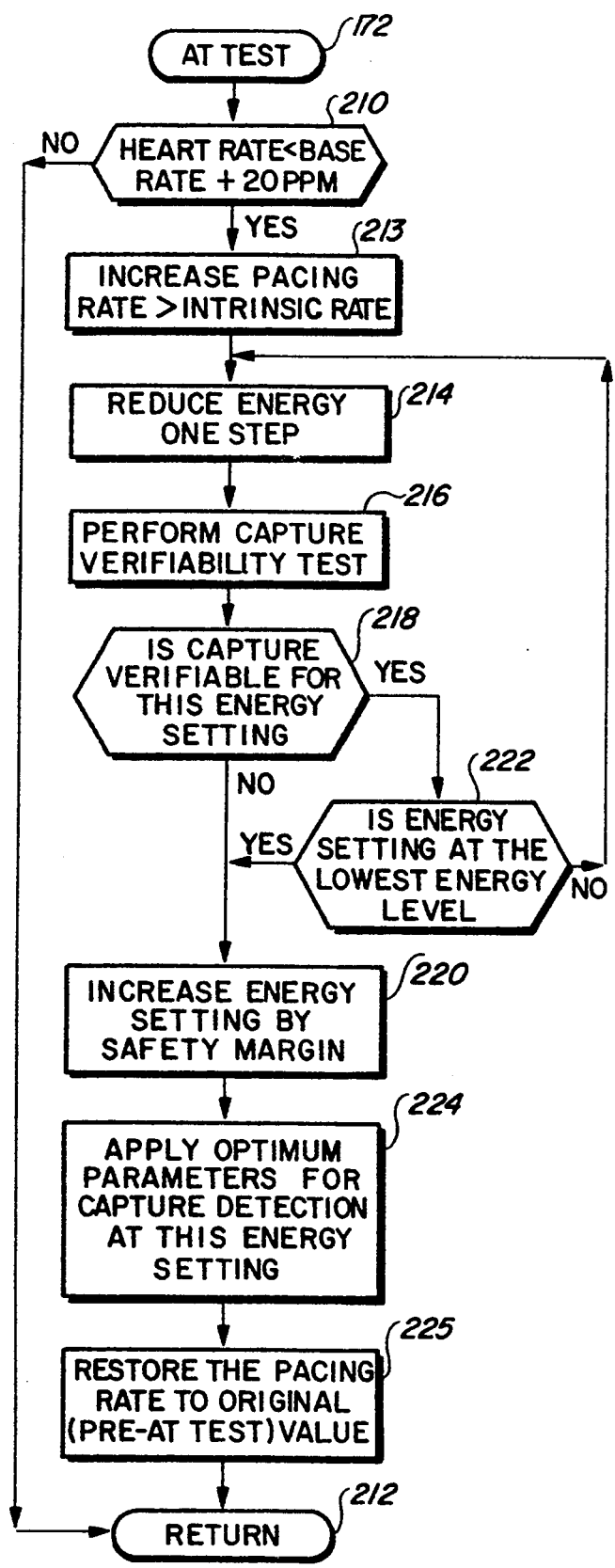
FIG. 11 shows a simplified flowchart of a autothreshold (AT) procedure carried out by the autocapture system shown in FIG. 9.

FIG. 11 shows a simplified flowchart of the AutoThreshold (AT) procedure carried out during the pacemaker autocapture operation shown in FIG. 9 (block 172). In accordance with such AutoThreshold procedure, a determination is made as to whether the heart rate is less than or equal to the programmed base rate plus 20 (block 210), If so, then the AutoThreshold process continues. If not, then the AutoThreshold procedure ends by returning (block 212) to the main autocapture routine (block 174 of FIG. 9).

If the heart rate is less than the programmed base rate plus 20 (as determined at block 210), then the pacing rate is increased to a rate greater than the intrinsic rate by increasing the pacing rate to the base rate plus 20 ppm (block 213). Then the stimulation energy is reduced one step (block 214). Here, "one step" refers to one step of the prescribed stimulation energy sequence, as defined, e.g., in a selected one of FIGS. 15-18, After reducing the stimulation energy one step, the capture verifiability test is performed (block 216) at the reduced stimulation energy. If capture is verifiable at the reduced energy setting, as determined at block 218, then a determination is made as to whether the energy has been reduced to its lowest energy level of the prescribed stimulation energy sequence (block 222). If not, then the process repeats (blocks 214, 216 and 218) at a further reduced energy setting.

Should the energy setting be at its lowest level (as determined at block 222), or should the capture not be verifiable at the current energy setting (as determined at block 218), then the energy is automatically increased by a prescribed safety margin (block 220) and the rate is restored to the base rate (block 225). In the preferred embodiment, the prescribed safety margin is three steps above the present energy setting, where one step is defined as one increment of the prescribed sequence of stimulation energies, e.g., as shown in FIGS. 15-18. The optimum sensitivity for evoked response detection is also programmed into the pacemaker (block 224). A detailed description of how to determine the optimum sensitivity is provided in conjunction with FIGS. 13A, 13B and 14.

Thus, as seen in FIG. 11, the AutoThreshold procedure sets the stimulation energy at an optimum level, just above that needed to effectuate capture. It does this by incrementally reducing the energy, one step at a time, until capture is no longer verifiable. Then, it increases the stimulation energy by the prescribed safety margin, e.g., three steps.

Figure 12:
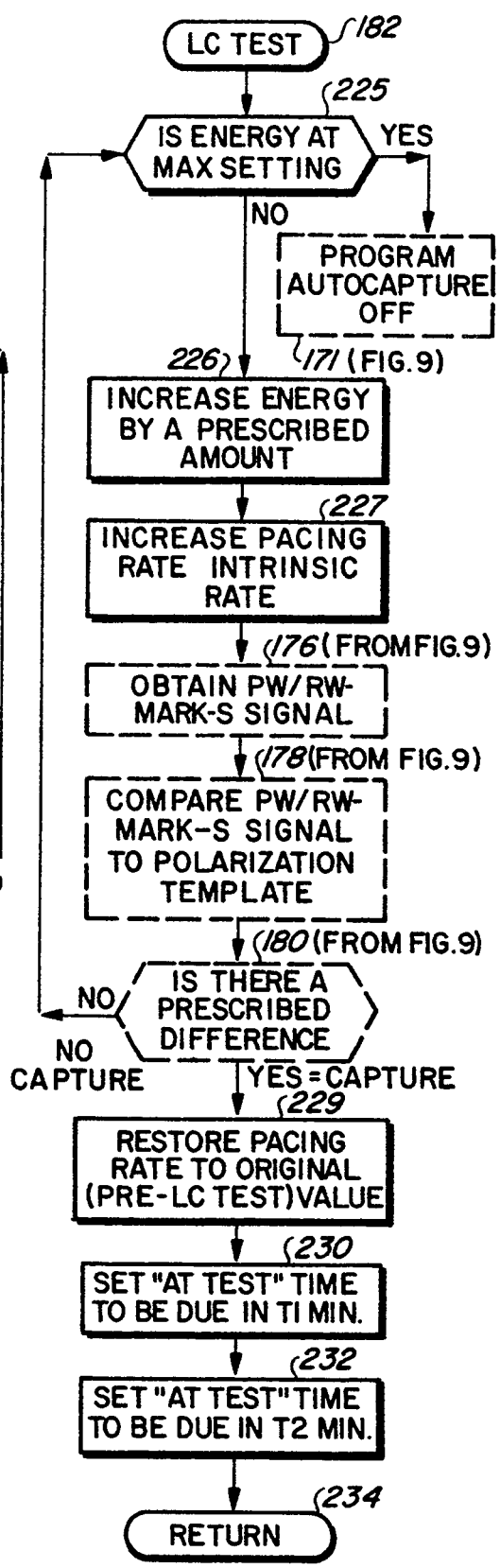
FIG. 12 shows a simplified flowchart of a loss-of-capture (LC) procedure carried out by the autocapture system shown in FIG. 9.

In FIG. 12, there is shown a simplified flowchart of the Loss-of-Capture (LC) procedure carried out during the pacemaker autocapture operation illustrated in FIG. 9 (block 182). The Loss-of-Capture procedure, once invoked, makes a preliminary determination as to whether the stimulation energy is at a maximum energy setting (block 225). If so, then capture verification is not possible, and the Loss-of-Capture procedure returns to the main autocapture program (block 171 of FIG. 9), and the autocapture function is automatically programmed OFF.

If the stimulation energy is not at a maximum energy setting (as determined at block 225), then the energy is increased a prescribed amount (block 226). The prescribed amount will be a programmable number of steps, preferably at least three steps, and on the selected energy sequence curve, e.g., as shown in FIGS. 15-18. Once the energy has been increased by the prescribed amount (block 226), then the pacing rate is again increased to a rate greater than the intrinsic rate by increasing the pacing rate to the base rate plus 20 ppm (block 227). Next, a determination is made as to whether capture exists at the increased energy. Such determination may be made by obtaining the PW/RW-Mark signal (block 176 of FIG. 9); comparing the multibit PW/RW-Mark-S signal to the appropriate Polarization template (block 178 of FIG. 9); and determining if there is a prescribed difference between the polarization template and the multibit PW/RW-Mark-S signal (block 180 of FIG. 9). If capture is not obtained, then the process repeats, by determining whether the energy is at a maximum setting (block 225) and, if not, increasing the energy a prescribed amount (block 226). If capture is obtained (as determined at block 180), then the pacing rate is restored to the base rate (block 229) and the time for performing the next AutoThreshold (AT) procedure is set to be due in T1 minutes (block 230), where T1 is a programmable number. Similarly, the time for performing the next AutoCalibration (AC) procedure is set to be due in T2 minutes (block 232), where T2 is a programmable number . The Loss-of-Capture (LC) routine then returns (block 234) to the main autocapture program (block 162 of FIG. 9).

Given that capture has been lost whenever the Loss-of-Capture procedure is invoked, and that some adjustments have been made to the stimulation energy, the time periods T1 and T2 will typically be relatively short, e.g., 2-5 minutes. However, once the AutoCalibration and AutoThreshold procedures have been performed after such T1 and T2 time periods, and assuming that such procedures verify that the stimulation energy is at an optimum level to maintain capture, then there is generally no need to perform the AutoCalibration and AutoThreshold procedures again for some time, e.g., once a day, unless capture is again lost.

Thus, it is seen that the LC procedure, which is invoked whenever a determination is made that capture has been lost, automatically increases the stimulation energy by a prescribed amount until capture is regained.

Figure 13A:
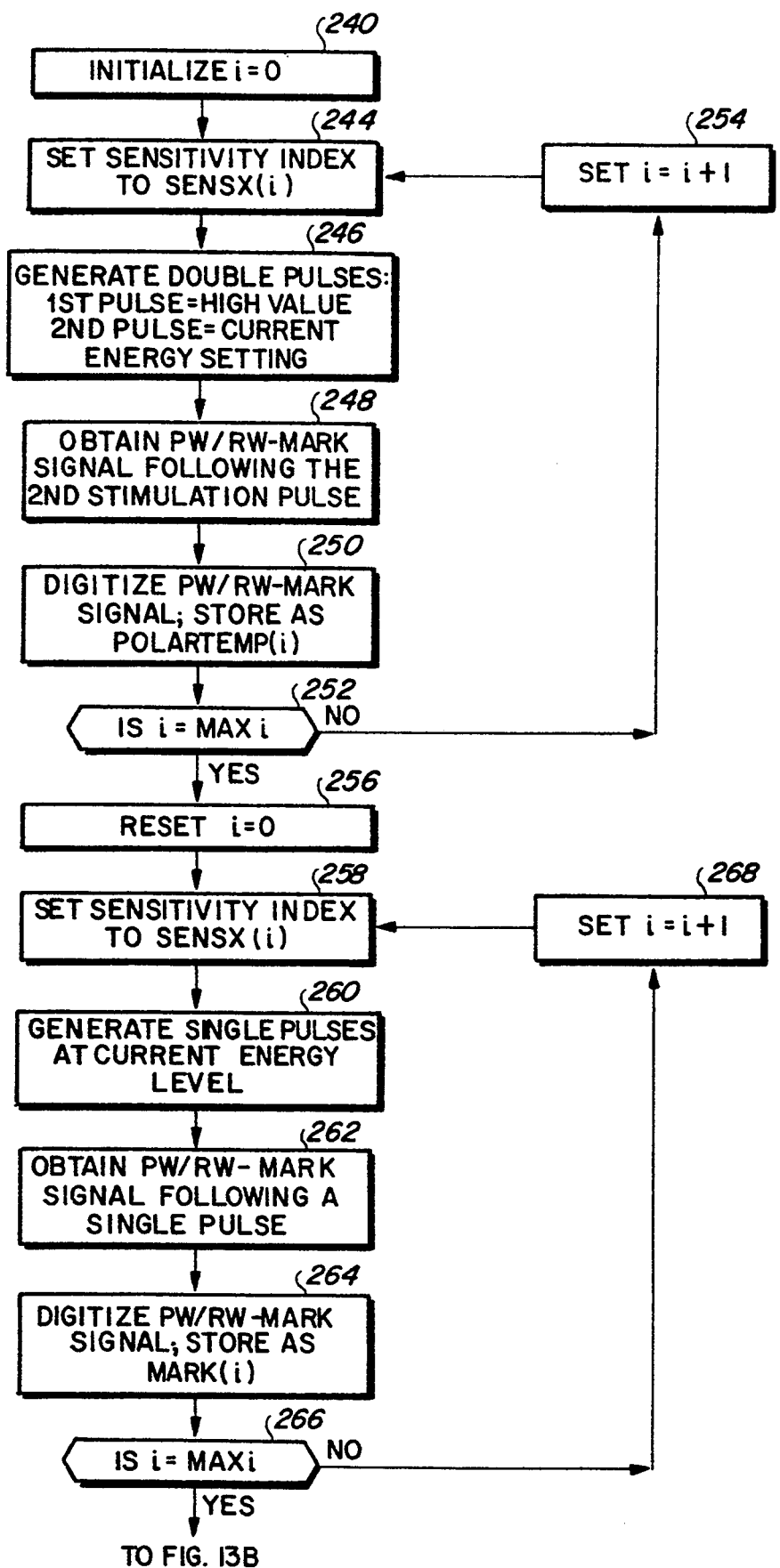
FIGS. 13A and 13B illustrates a simplified flowchart of a capture verifiability test carried out in accordance with the present invention.
Figure 13B:
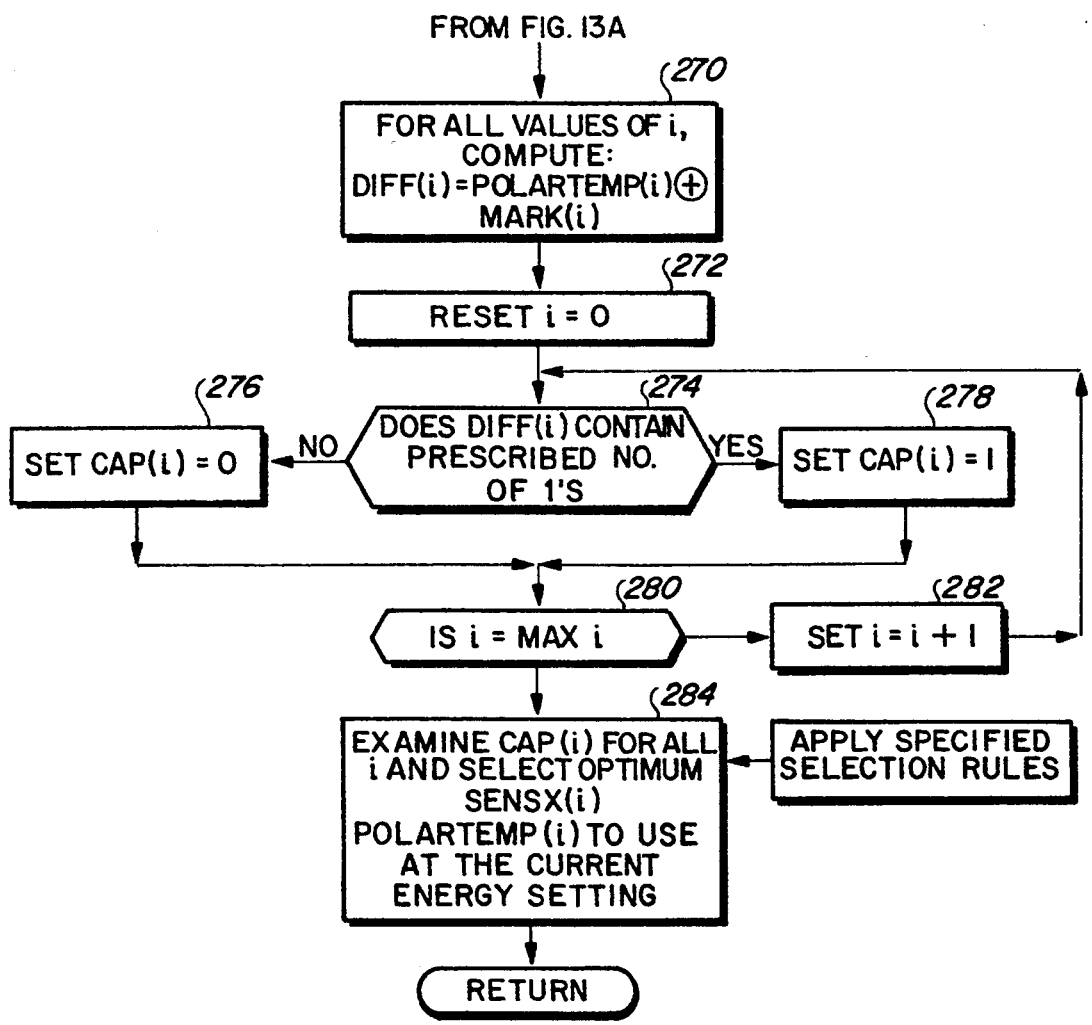
Figure 15:
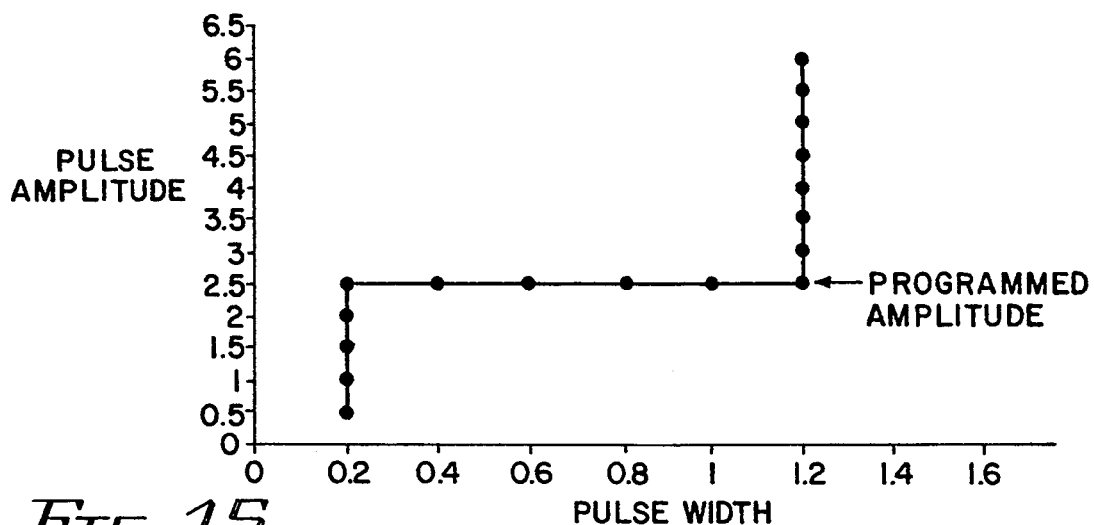
FIGS. 15, 16, 17 and 18 show representative search curves for pulse width, amplitude, and pulse width/amplitude autothreshold search modes, respectively, used by the autocapture system of the invention.
Figure 16:
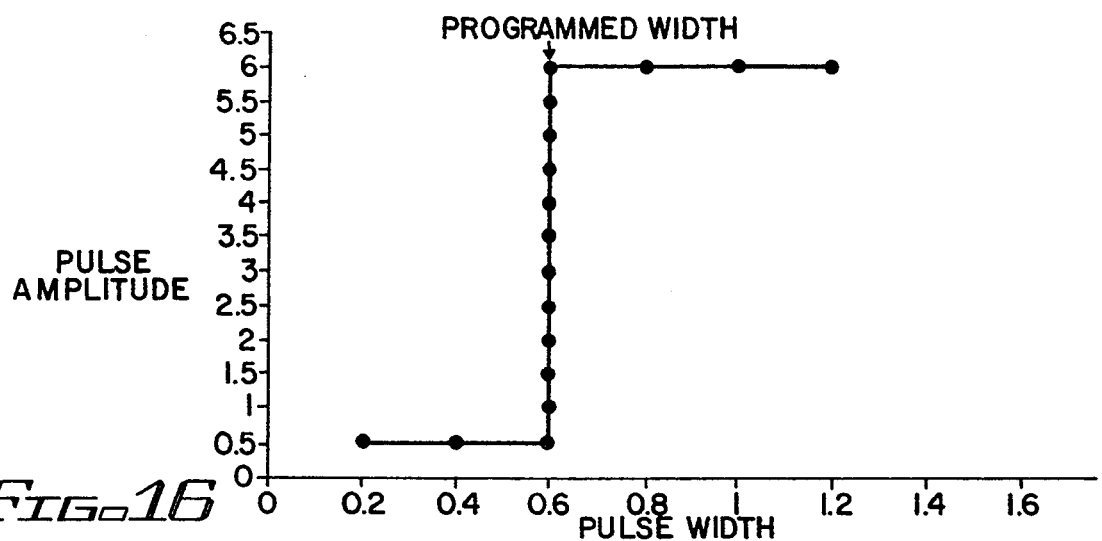

FIGS. 13A and 13B illustrate a simplified flowchart of the preferred manner of carrying out the capture verifiability test used in both the AutoCalibration and AutoThreshold procedures described above in conjunction with FIGS. 10A and 11. Such capture verifiability test assumes a digital approach, i.e., assumes that the polarization template and the PW/RW-Mark signals are appropriately digitized, as described above. The test starts, as indicated in FIG. 13A, by initializing an index value, i, to a prescribed starting point, e.g. zero (block 240). The index value is used to keep track of the various sensitivity settings that may accompany each energy setting. (Note that to ensure 100% pacing during this test, the rate has already been increased above the intrinsic rate at block 193 of FIG. 10A.) Next, the sensitivity index is set to a value, Sensx(i). The sensitivity index is a convenient number that corresponds to the possible sensitivity settings of the sense amplifiers (84 and 90, FIG. 3) used to sense the evoked response of the heart in providing the PW/RW-Mark signal. Thus, while the sensitivity settings of the sense amplifier may be, e.g., 2 mV; 4 mV; 6 mV; 8 mV; 10 mV; etc., the sensitivity indexes associated with such numbers may simply be 0, 1, 2, 3, 4, etc. The heart is then paced using a double stimulation pulse at the current energy setting at block 246. The first pulse is a pulse of high energy, and is used to ensure that capture is obtained. The second pulse, which follows the first pulse by a programmed amount, e.g., 100 msec, is a pulse of the current energy setting. The first pulse captures the heart. The second pulse cannot capture the heart because it occurs during the heart's refractory period wherein the heart is incapable of being captured. Thus, the only response possible from the second pulse is that due to lead polarization. The response to the second pulse is thus obtained as the PW/RW-Mark signal for the polarization artifact (block 248). This signal is then digitized (block 250), and stored as a signal referred to as the PolarTemp(i), representing the polarization template for the sensitivity setting corresponding to the index value, i, at the current energy setting.

A determination is next made as to whether the sensitivity index is at its maximum value (block 252). If not, it is incremented by one (block 254) and the process continues (blocks 244, 246, 248 250 and 252). In this manner, a set of polarization templates is obtained, with each polarization template in the set corresponding to one of the sensitivity settings used with the current energy setting.

Once the complete set of polarization templates has been obtained, the index value, i, is reset (block 256). The sensitivity index is then set to Sensx(i) (block 258), and the heart is paced with a single pulse at the current stimulation energy (block 260). The resulting PW/RW-Mark signal from the single stimulation pulse is obtained (block 262). Such signal is digitized and stored as a signal Mark(i). Appropriate Mark(i) signals are similarly obtained for all possible values of the sensitivity index (blocks 266, 268, 258, 260, 262 and 264). Once all of the Mark(i) signals have been obtained, the capture verifiability test continues (in FIG. 13B) by computing the Exclusive OR difference between the PolarTemp(i) and Mark(i) signals for all index value, i. Such difference is stored as a signal DIFF(i) (block 270). The Exclusive OR difference compares the individual bits of the PolarTemp(i) and Mark(i) signals on a bit-by-bit basis, and sets a corresponding bit of the DIFF(i) signal to a "0" if there is no difference between the compared bits, and to a "1" if there is a difference.

Once the DIFF(i) signal has been obtained for all index value, i, the sensitivity index value, i, is again reset to its initial value (block 272). The DIFF(i) signal is examined to determine if it contains a prescribed number of bits that are set (block 274). If so, then a capture signal, Cap(i), is set to a "1" (block 278); if not, then Cap(i) is set to a "0" (block 276). A Cap(i) signal that is "1" indicates that capture has occurred at the corresponding Sensx(i) sensitivity setting for the current energy setting; whereas a Cap(i) signal that is "0" indicates that capture has not occurred at the Sensx(i) sensitivity setting. This process continues for all index values, i (blocks 280, 282, 274, 276 and 278). For example, assuming a DIFF(i) signal that is 16 bits long, the prescribed number of bits that must be set before the Cap(i) signal is set to "1" may be four (4). For a DIFF(i) signal that is eight bits long, the prescribed number of bits that must be set before the Cap(i) signal is set to "1" is at least one bit, and preferably three bits for improved noise immunity.

Once the Capture Verification signal, Cap(i), has been obtained for all index values, i, such signal is examined over all index values, i, to select an optimum sensitivity setting and corresponding polarization template for use at the current energy setting (block 284). Such determination is made based upon specified selection rules. The specified selection rules may dictate, for example, that if capture is verifiable (Cap(i)=1) for only one value of i out of all the possible values of i, then the sensitivity setting and the polarization template (Sensx(i) and PolarTemp(i), respectively) corresponding to that index value, i, are the optimum settings. If capture is verifiable (Cap(i)=1) for two or more values of i, then the optimum value of Sensx(i) and PolarTemp(i) is that value corresponding to the difference signal, Diff(i), having the maximum number of bits set to "1"(i.e., the signal which has the best signal-to-noise ratio, or the best "signal-to-polarization" ratio). If the difference signal, Diff(i), has two or more values of i which also have the same number of bits set to "1", then the optimum value of Sensx(i) and PolarTemp(i) is that value corresponding to the Diff(i) signal having the maximum number of bits with the highest sensitivity setting.

FIG. 14 depicts an example of the type of data used and generated in carrying out the capture verifiability test of FIGS. 13A and 13B, and the AutoCalibration procedure of FIG. 11. (Note that the capture verifiability test performs capture verifiability at all possible sensitivity settings for only one stimulation energy. The AutoCalibration procedure then repeats the capture verifiability test for all energy settings of interest as defined by the prescribed sequence of energy settings.) The data shown in FIG. 14 assumes that an eight-bit polarization template and multibit PW/RW-Mark-S signals are used. Such eight bit signals are used for illustration purposes only, as the preferred number of bits in the polarization template and multibit PW/RW-Mark-S is at least 15.

As seen in FIG. 14, at an energy setting of 0.5 volts pulse amplitude (PA) and 0.2 msec pulse width (PW), eight sensitivity index values, 0–7(having values of 30, 25, 15, 10, 8, 6, 4 and 2 mV, respectively) are available. The polarization template, PolarTemp(i), for an index value, i, of "0" and "1" is "00000000". The corresponding Mark(i) signals for these same index values of i is "00000000" and "00001000", respectively. Comparing these signals on a bit-by-bit basis, it is seen that the DIFF(i) signal (which is formed by taking the Exclusive OR function of the PolarTemp(i) signal with the Mark(i) signal) for these same index values of i is "00000000" and "00001000", respectively. Using a capture determining rule that at least three bits must be set in the DIFF(i) signal before a determination of capture exists, the corresponding Cap(i) signal for these same index values of i is "0" and "0", i.e., capture does not occur.

At this same stimulation energy, it is seen for the example shown in FIG. 14 that at the sensitivity index settings of i=2, 3 and 4, the DIFF(i) signal corresponding to these values of PolarTemp(i) and Mark(i) is thus computed to be "01110000", "01010110" and "00110100", respectively. Each of these DIFF(i) signals has at least three bits that are set, indicating that at least three bits are different between the corresponding PolarTemp(i) signal and the Mark(i) signals. Hence, using the rule that at least three bits different is sufficient to indicate capture, the Cap(i) signal for these three values of i is set to "1". The optimum value of Sensx(i) and PolarTemp(i) is that value corresponding to the difference signal, Diff(i), having the maximum number of bits set to "1", i.e., i=3. Thus, whenever this stimulation energy is selected, the sensitivity index is automatically set to 3, resulting in a polarization template of "01100110". As a second example, capture is verifiable (Cap(i)=1) at a pulse amplitude of 1.5 volts and 0.2 msec for the sensitivity index settings of i=1 and 2 and each Diff(i) signal has an equal number of bits set to "1". In this case, the optimum value of Sensx(i) and PolarTemp(i) is that value corresponding to the difference signal, Diff(i), having the the maximum number of bits (3) with the highest sensitivity, i.e., i=2. It is submitted that those of skill in the programming arts can readily fashion appropriate code in order to implement the procedures and routines described above in connection with FIGS. 9-13 for execution by an appropriate processor or other control logic within an implantable pacemaker.

Figure 17:
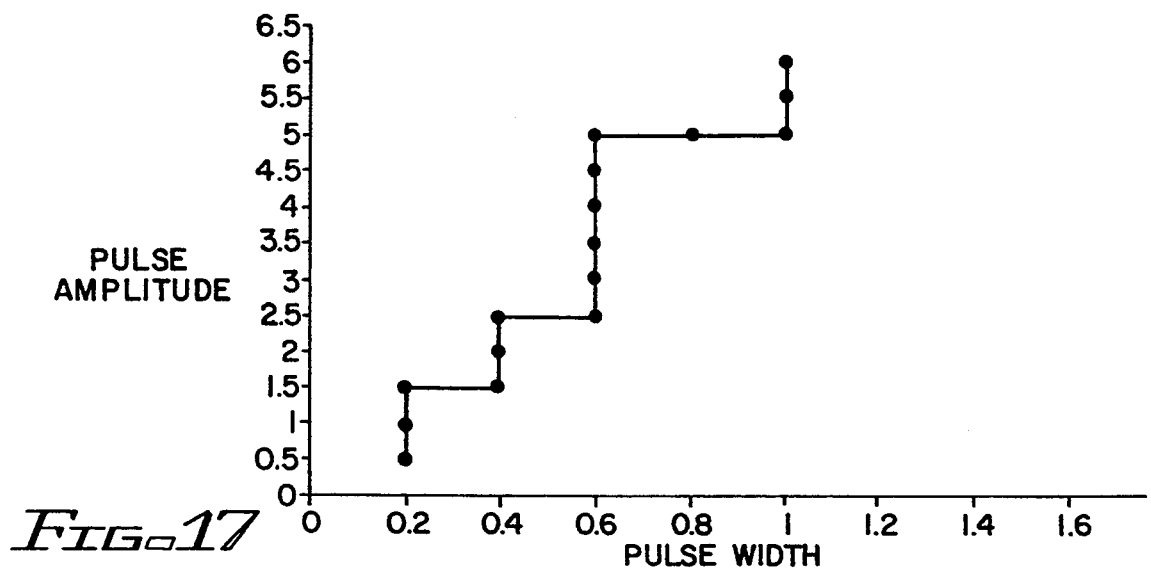
Figure 18:
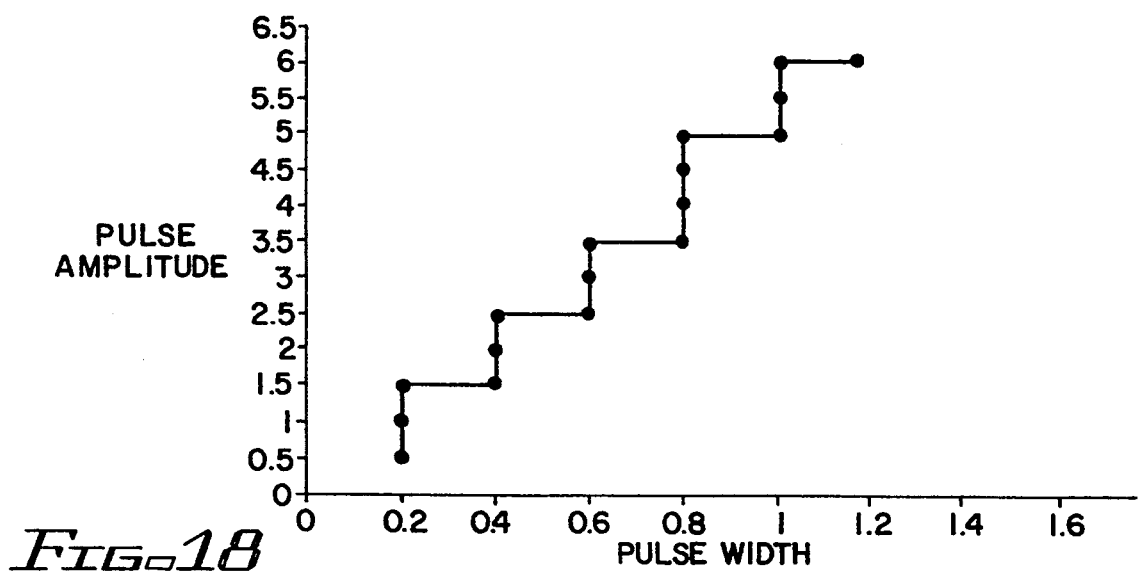

As indicated above, FIGS. 15-18 show representative curves of stimulation energy, showing both pulse width, amplitude, and pulse width/amplitude variations. Such curves thus represent a prescribed stimulation energy sequence that may be followed when adjusting the stimulation energy to an optimum value, e.g., as is done in carrying out the AutoThreshold routine of FIG. 11; or when increasing the stimulation energy when capture is lost. Each dot on the curves represents a different "step" in the stimulation energy. Thus, for example, if the curve shown in FIG. 17 is used, and if the current stimulation energy is 1.5 volts at 0.4 msec, and if the stimulation energy is to be increased three steps, the stimulation energy would increase to 2.5 volts at 0.6 msec. It should be noted that FIGS. 15-18 are only three possible stimulation energy curves and it is understood that other curves may be employed without deviating from the spirit of the invention.

As described above, it is thus seen that the present invention provides a way to determine whether a given stimulation pulse generated by a pacemaker has effectuated capture. Further, it is seen that the invention provides a system and/or method for adjusting the energy of a stimulation pulse to an appropriate level that provides sufficient energy to effectuate capture, but does not expend any significant energy beyond that required to effectuate capture, thereby always pacing with a safety margin that is not excessively large.

As seen from the above description, it is also seen that the invention provides an implantable pacemaker that includes circuitry for regularly checking the capture-determining threshold and adjusting the stimulation pulse energy and sensitivity settings accordingly so that energy is not needlessly wasted in a safety margin that is excessively large.

As also described above, it is seen that the invention provides a technique for clearly detecting and distinguishing an evoked response from other signals that may occur at the same time as an evoked response, but are not an evoked response.

As further described above, it is seen that the invention advantageously provides a technique for eliminating, or at least minimizing, the adverse effect that lead polarization has on the ability of the pacemaker sensing circuits to sense an evoked response.

Moreover, as described above, it is seen that through use of the invention, the evoked response signal can be reliably sensed even when inextricably intertwined with a difficult-to-characterize polarization signal.

While the invention herein disclosed has been described by means of specific embodiments and applications thereof, numerous modifications and variations could be made thereto by those skilled in the art without departing from the scope of the invention set forth in the claims.

What is claimed is:

1. A system for detecting capture in an implantable pulse generator on a beat-by-beat basis, the implantable pulse generator being coupled to an implantable stimulation lead in contact with the heart, the system comprising:
    pulse generating means for generating stimulation pulses at a desired stimulation pulse energy;
    sensing means, coupled to the stimulation lead, for sensing cardiac signals and for sensing post-stimulation signals which occur following each stimulation pulse, the sensing means including means for sensing first and second post-stimulation signals at each of a plurality of sensitivities, the first post-stimulation signals corresponding to polarization signals sensed at each of a plurality of sensitivities;
    means for comparing the first and second post-stimulation signals at each respective sensitivity and producing as an output a plurality of difference signals, presence of a prescribed difference signal indicating that the heart was captured by the stimulation pulse;
    means for determining an optimum sensitivity setting based on the prescribed difference signal, and for biasing the sensing means to the optimum sensitivity setting for stimulation pulses subsequently generated at the desired stimulation pulse energy; and
    processing means for comparing post-stimulation signals sensed by the sensing means at the optimum setting with the respective polarization signal, whereby a prescribed difference signal sensed by the sensing means at the optimum sensitivity setting is used for capture detection on a beat-by-beat basis.

2. The system for detecting capture, as set forth in claim 1, wherein:
    the pulse generating means includes means for generating stimulation pulses at a plurality of stimulation pulse energies;
    the sensing means senses each of the first and second signals at each of the plurality of sensitivities at each of the plurality of stimulation pulse energies; and
    the determining means determines the optimum sensitivity setting for each of the plurality of stimulation pulse energies based on the occurrence of the prescribed difference signal.

3. The system for detecting capture, as set forth in claim 2, further comprising:
    means for detecting when the prescribed difference signal no longer exists, the absence of the prescribed difference signal indicating that capture has been lost;

adjusting means for repeatedly increasing the energy of the stimulation pulse in prescribed energy steps until the presence of the prescribed difference signal is found indicating that the heart was captured by the stimulation pulse and for adding a prescribed safety margin thereto; and means for changing the sensitivity setting of the sensing means to the optimum sensitivity setting determined by the determining means for stimulation pulses subsequently generated by the pulse generating means.

4. The system for detecting capture, as set forth in claim 2, further comprising:

adjusting means for repeatedly decreasing the energy of the stimulation pulse in prescribed energy steps;

means for changing the sensitivity setting of the sensing means to the optimum sensitivity setting determined by the determining means for each energy step; and means for detecting when the prescribed difference signal no longer exists, the absence of the prescribed difference signal indicating that capture has been lost, whereupon the adjusting means increases the stimulation energy by a prescribed safety margin.

5. The system for detecting capture, as set forth in claim 1, wherein the sensing means comprises:

a comparator which has as an output a first value if the magnitude of the post-stimulation signal is less than a prescribed reference value, and a second value if the magnitude of the post-stimulation signals is greater than the prescribed reference value.

6. The system for detecting capture, as set forth in claim 5, wherein the sensing means further comprises:

means for sampling the output of the comparator at least eight times during a prescribed sampling window following the delivery of the stimulation pulse to the heart, the sampling means producing as an output a digital signature having at least eight bits, with each bit of the digital signature corresponding to the value of the output of the comparator at a different sampling time.

7. The system for detecting capture, as set forth in claim 6, wherein the prescribed difference signal comprises a difference signal having a maximum number of bits.

8. The system for detecting capture, as set forth in claim 7, wherein the desired stimulation pulse energy has associated therewith a plurality of prescribed difference signals which have an equal number of bits, the determining means further comprising:

means for analyzing the plurality of prescribed difference signals which have the equal number of bits and for selecting as the optimum sensitivity setting that setting which corresponds to the highest sensitivity setting.

9. The system for detecting capture, as set forth in claim 7, wherein the prescribed difference signal comprises at least three bits.

10. The system for detecting capture, as set forth in claim 1, further comprising:

means for stimulating the heart with a first and a second stimulation pulse separated in time by an interval less than a refractory period of the heart, the first stimulation pulse having a stimulation energy sufficient to capture the heart, the second stimulation pulse having the desired stimulation pulse energy; and wherein the sensing means includes means for sensing a post-stimulation signal in response to the second pulse at each of the plurality of sensitivities, the post-stimulation signals sensed in response to the second pulse corresponding to the first post-stimulation signal sensed at each of the plurality of sensitivities.

11. The system for detecting capture, as set forth in claim 10, wherein the sensing means includes means for digitizing the first post-stimulation signal in response to the second stimulation pulse, and for digitizing the second post-stimulation signal in response to the desired stimulation pulse.

12. The system for detecting capture, as set forth in claim 11, wherein the digitizing means includes:

means for defining a multi-bit word, each bit of the multi-bit word indicating whether the magnitude of the post-stimulation signal is greater or less than a prescribed threshold at a particular sample time following the delivery of the stimulation pulse to the heart, a first multi-bit word being thus formed comprising the first post-stimulation signal, and a second multi-bit word being thus formed in response to the second post-stimulation signal.

13. The system for detecting capture, as set forth in claim 12, wherein the means for comparing the first and second post-stimulation signals at each respective sensitivity includes means for comparing corresponding bits of the first and second multibit words and indicating capture only when at least a prescribed number of the bits are different.

14. The system for detecting capture, as set forth in claim 13, wherein the first and second multi-bit words each include at least eight bits, and wherein the number of bits that must be different between the first and second multi-bit words in order to indicate capture comprises at least three.

15. The system for detecting capture, as set forth in claim 12, wherein the means for digitizing the sensed post-stimulus signal includes:

means for sampling the magnitude of the first and second sensed post-stimulus signals at a plurality of sample times and representing the sampled magnitude as a digital word having a plurality of bits at each sample time, a first digital word being formed from sampling the sensed post-stimulus signal at a first sample time, a second digital word being formed from sampling the sensed post-stimulus signal at a second sample time, and so on, with a digital signature being formed that comprises the combination of all of the digital words from all of the sample times, the digital signature being representative of the digitized sensed post-stimulus signal;

whereby a first post-stimulus signature is formed by digitizing the first post-stimulus signal following delivery of the second stimulation pulse and the second post-stimulus signal following delivery of the desired stimulation pulse.

16. The system for detecting capture, as set forth in claim 15, wherein the means for comparing the first and second post-stimulus signals comprises comparing the first post-stimulus signal signature with the second post-stimulation signal on a digital word by digital word basis, and indicating capture only when a prescribed difference exists between a prescribed number of the digital words.

17. An autocapture system for use within an implantable pulse generator, comprising:
   means for stimulating the heart with a stimulation pulse at each of a plurality of stimulation energies;
   sensing means for sensing cardiac signals and for sensing post-stimulation signals which occur following each stimulation pulse, the post-stimulation signals being sensed at each of a plurality of sensitivity settings for each of the plurality of stimulation energies;
   means for defining a plurality of polarization templates corresponding to the plurality of post-stimulation signals;
   processing means for comparing the plurality of post-stimulation signals with the corresponding polarization template and indicating capture if a prescribed difference exists therebetween, and for determining an optimal sensitivity setting for the sensing means for each of the plurality of stimulation energies based on the existence of the prescribed difference signal;
   means for biasing the sensing means at the optimum sensitivity setting for stimulation pulses subsequently generated at a desired stimulation pulse energy; and
   wherein the processing means compares the post-stimulation signal sensed by the sensing means at the optimum sensitivity setting to the corresponding polarization template for beat-by-beat capture detection, whereby the presence of the prescribed difference signal at the optimum sensitivity setting indicates whether capture has occurred.

18. The autocapture system, as set forth in claim 17, further comprising:
   means for detecting when the prescribed difference signal no longer exists, the absence of the prescribed difference signal indicating that capture has been lost;
   adjusting means for repeatedly increasing the energy of the stimulation pulse in prescribed energy steps until the presence of the prescribed difference signal is found indicating that the heart was captured by the stimulation pulse and for adding a prescribed safety margin thereto; and
   means for changing the sensitivity setting of the sensing means to the optimum sensitivity setting determined by the processing means for the stimulation pulses subsequently generated by the pulse generating means.

19. The autocapture system, as set forth in claim 17, further comprising:
   adjusting means for repeatedly decreasing the energy of the stimulation pulse in prescribed energy steps;
   means for changing the sensitivity setting of the sensing means to the optimum sensitivity setting determined by the processing means for each energy step; and
   means for detecting when the prescribed difference signal no longer exists, the absence of the prescribed difference signal indicating that capture has been lost, whereupon the adjusting means increases the stimulation energy by a prescribed safety margin.

20. The autocapture system, as set forth in claim 17, wherein the means for defining the plurality of polarization templates comprises:
   means for stimulating the heart with a first and a second stimulation pulse separated in time by an interval less than a refractory period of the heart, the first stimulation pulse having a stimulation energy sufficient to capture the heart, the second stimulation pulse having the desired stimulation energy;
   wherein the sensing means includes means for sensing a post-stimulation signal in response to the second pulse at the plurality of sensitivities, the post-stimulation signals sensed in response to the second pulse being the plurality of polarization templates.

21. A method for detecting capture in an implantable pulse generator, the method comprising the steps of:
   generating stimulation pulses at a desired stimulation pulse energy;
   sensing cardiac signals and post-stimulation signals which occur following each stimulation pulse with a sense amplifier, the post-stimulation signals including first and second post-stimulation signals at each of a plurality of sensitivities, the first post-stimulation signals corresponding to polarization signals sensed at each of a plurality of sensitivities;
   comparing the first and second post-stimulation signals at each respective sensitivity and producing as an output a plurality of difference signals, presence of a prescribed difference signal indicating that the heart was captured by the stimulation pulse;
   determining an optimum sensitivity setting based on the prescribed difference signal;
   biasing the sense amplifier to the optimum sensitivity setting for stimulation pulses subsequently generated at the desired stimulation pulse energy; and
   comparing post-stimulation signals sensed at the optimum setting with the respective polarization signal, whereby a prescribed difference signal sensed by the sensing means at the optimum sensitivity setting is used for capture detection on a beat-by-beat basis.

22. The method, as set forth in claim 21, further comprising the steps of:
   generating stimulation pulses at a plurality of stimulation pulse energies;
   sensing each of the first and second post-stimulation signals at each of the plurality of stimulation pulse energies; and
   determining the optimum sensitivity setting for the sensing means for each of the plurality of stimulation pulse energies based on the occurrence of the prescribed difference signal.

23. The method, as set forth in claim 21, wherein the defining step comprises the steps of:
   stimulating the heart with a first stimulation pulse having a stimulation energy sufficient to capture the heart;
   stimulating the heart with a second stimulation pulse having a desired stimulation energy during a refractory period of the heart; and
   sensing post-stimulation signals in response to the second pulse at each of the plurality of sensitivities corresponding to the polarization signals at each of the plurality of sensitivities.

24. The method, as set forth in claim 21, further comprising the steps of:
   detecting when the prescribed difference signal no longer exists, the absence of the prescribed difference signal indicating that capture has been lost;

repeatedly increasing the energy of the stimulation pulse in prescribed energy steps until the presence of the prescribed difference signal is found indicating that the heart was captured by the stimulation pulse; and changing the sensitivity setting of the sensing means to the optimum sensitivity setting for stimulation pulses subsequently generated.

25. The method, as set forth in claim 21, further comprising the steps of:

repeatedly decreasing the energy of the stimulation pulse in prescribed energy steps using an adjusting means;

changing the sensitivity setting of the sensing means to the optimum sensitivity setting determined by the determining means for each energy step; and detecting when the prescribed difference signal no longer exists, the absence of the prescribed difference signal indicating that capture has been lost, whereupon the adjusting means increases the stimulation energy by a prescribed safety margin.

26. A method for determining capture within an implantable pulse generator, the implantable pulse generator including stimulation means for generating a stimulation pulse at a selectable stimulation energy and delivering the stimulation pulse to a heart, and sensing means for sensing a post-stimulus signal from the heart at a selectable sensitivity following delivery of the stimulation pulse, the method comprising the steps of:

(a) defining a plurality of polarization templates for a selected stimulation energy of the stimulation means and for a plurality of sensitivity settings of the sensing means;

(b) stimulating the heart with a stimulation pulse having the selected stimulation energy;

(c) sensing a plurality of post-stimulus signals at the selected stimulation energy with the sensing means at each of the plurality of sensitivity settings;

(d) comparing the polarization template with the post-stimulus signal and indicating capture if a prescribed difference signal exists therebetween; and (e) determining an optimum sensitivity setting for the sensing means based on the prescribed difference signal.

27. The method for determining capture, as set forth in claim 26, wherein step (a) comprises:

(1) stimulating the heart with a pair of stimulation pulses separated in time by an interval less than a refractory period of the heart, a first pulse of the pair of stimulation pulses having a stimulation energy sufficient to capture the heart, a second pulse of the pair of stimulation pulses having the selected stimulation energy;

(2) sensing the post-stimulus signal from the heart in response to the second pulse at each of the plurality of sensitivity settings; and (3) defining the polarization template as the post-stimulus signal sensed in step (2).

28. The method for determining capture, as set forth in claim 26, further comprising the steps of:

(f) digitizing the plurality of sensed post-stimulus signals at the selected stimulation energy; and (g) digitizing the plurality of sensed post-stimulus signal obtained from the second pulse of the pulse pair.

29. The method for determining capture, as set forth in claim 28, wherein the steps of digitizing the sensed post-stimulus signals in steps (f) and (g) comprises:

defining a multibit word, each bit of the multibit word indicating whether the magnitude of the post-stimulus signal was greater or less than a prescribed threshold at a particular sample time following the delivery of the stimulation pulse to the heart, a first multibit word being thus formed representing the post-stimulus signal at the selected stimulation energy, and a second multibit word being thus formed representing the polarization template.

30. The method for determining capture, as set forth in claim 29, wherein step (d) comprises comparing corresponding bits of the first and second multibit words and indicating capture only when at least a prescribed number of the bits are different.

31. The method for determining capture, as set forth in claim 30, wherein the first and second multibit words each include at least eight bits, and wherein the number of bits that must be different between the first and second multibit words comprises at least three.

32. The method for determining capture, as set forth in claim 28, wherein the step of digitizing the sensed post-stimulus signal comprises sampling the magnitude of the sensed post-stimulus signal at a plurality of sample times and forming a digital word having a plurality of bits at each sample time, a first digital word being formed from sampling the sensed post-stimulus signal at a first sample time, a second digital word being formed from sampling the sensed post-stimulus signal at a second sample time, and so on, with a digital signature being formed that comprises the combination of all of the digital words from all of the sample times; the digital signature being representative of the digitized sensed post-stimulus signal; a first digital signature being formed by thus digitizing the post-stimulus signal following delivery of the stimulation pulse, the first digital signature comprising an post-stimulus signal signature; and a second digital signature being formed by thus digitizing the post-stimulus signal following delivery of the second stimulation pulse of the pair of stimulation pulses, the second digital signature comprising a polarization template signature.

33. The method for determining capture, as set forth in claim 32, wherein step (d) comprises comparing the post-stimulus signal signature with the polarization template signature and indicating capture only when a prescribed difference exists therebetween.

34. The method for determining capture, as set forth in claim 33, wherein the comparison of the post-stimulus signal signature to the polarization template signature comprises comparing the signatures on a digital word by digital word basis, and indicating capture only when a prescribed difference exists between a prescribed number of the digital words.

* * * * *